United States Patent
Wang

(10) Patent No.: US 9,109,992 B2
(45) Date of Patent: Aug. 18, 2015

(54) METHOD FOR STRENGTHENING A WELLBORE OF A WELL

(75) Inventor: Hong Wang, Cypress, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 562 days.

(21) Appl. No.: 13/488,062

(22) Filed: Jun. 4, 2012

(65) Prior Publication Data

US 2013/0143777 A1  Jun. 6, 2013

Related U.S. Application Data

(60) Provisional application No. 61/495,898, filed on Jun. 10, 2011.

(51) Int. Cl.
| | | |
|---|---|---|
| *E21B 43/267* | (2006.01) | |
| *G01N 19/08* | (2006.01) | |
| *E21B 33/138* | (2006.01) | |
| *G06F 17/00* | (2006.01) | |
| *B82Y 99/00* | (2011.01) | |

(52) U.S. Cl.
CPC .............. *G01N 19/08* (2013.01); *E21B 33/138* (2013.01); *E21B 43/267* (2013.01); *G06F 17/00* (2013.01); *B82Y 99/00* (2013.01)

(58) Field of Classification Search
CPC .............................. E21B 33/138; E21B 43/267
USPC ............................................ 166/250.1, 253.1
See application file for complete search history.

(56) References Cited

U.S. PATENT DOCUMENTS

| | | | | |
|---|---|---|---|---|
| 3,845,824 | A | * | 11/1974 | Tinsley ..................... 166/308.2 |
| 4,848,461 | A | * | 7/1989 | Lee ............................ 166/250.1 |
| 5,241,475 | A | | 8/1993 | Lee et al. |
| 6,790,812 | B2 | | 9/2004 | Halliday et al. |
| 7,900,504 | B2 | | 3/2011 | Huynh et al. |
| 2005/0222852 | A1 | | 10/2005 | Craig |
| 2009/0221452 | A1 | | 9/2009 | Whitfill et al. |
| 2010/0181073 | A1 | | 7/2010 | Dupriest et al. |
| 2010/0230164 | A1 | | 9/2010 | Pomerleau |

OTHER PUBLICATIONS

PCT Office; Written Opinion of the International Search Authority; Sep. 24, 2012; Alexandria, Virginia.
Hong (Max) Wang; Is your mud a fracturing fluid or a non-fracturing fluid?; AADE; Apr. 10-11, 2012; 1pg.; USA.
Mark W. Alberty, Michael R. McLean; A physical model for stress cages; SPE International; Sep. 26-29, 2004; p. 1-8; USA.
M.A. Dick, T.J. Heinz, C.F. Svoboda, M. Aston; Optimizing the selection of bridging particles for reservoir drilling . . . ; SPE International; Feb. 23-24, 2000; p. 1-8; USA.

* cited by examiner

*Primary Examiner* — Zakiya W Bates
*Assistant Examiner* — Silvana Runyan
(74) *Attorney, Agent, or Firm* — Haynes and Boone, LLP

(57) ABSTRACT

One of the challenges of modern hydrocarbon production is the efficient sealing of a lost circulation zone. It has been discovered that it is possible to efficiently seal the fractures of lost circulation zones by formulating a fracture sealing composition based on a width of the fracture. In particular, it has been found that when the spurt loss volume is less than or equal to the fracture volume capacity of the fracture, then the sealing fluid can be pumped into the wellbore to form a sealing relationship with the fracture.

19 Claims, 7 Drawing Sheets

Figure 6. A Relationship between the Unit Slot Length Spurt Loss Volume and the Concentration of a Particulate Sealing Composition in a Fluid Bridging with large particulates (1002) first Further plugging with small particulates (1008)

METHOD FOR STRENGTHENING A WELLBORE OF A WELL

CROSS-REFERENCE TO RELATED APPLICATIONS

This application claims priority and benefit of provisional application Ser. No. 61/495,898 entitled Method For Strengthening A Wellbore Of A Well filed Jun. 10, 2011 and which is incorporated in its entirety by reference herein.

FIELD

The present invention relates to drilling, cementing, completing and workover of wells through a subterranean formation. More specifically, the present invention relates to a method of increasing the pressure containment of a wellbore during engineering operations of the well.

BACKGROUND

A multitude of wells have been drilled into various subterranean formations for the exploration and extraction of oil, gas, and other material therefrom. Typically, these wells are constructed through the utilization of a rotary drilling system including a plurality of connected drill pipe commonly referred to as the drill string, operatively connected to a rotary drill bit. As the rotary drill bit drills through the subterranean formation, drilling fluid is pumped from a pumping unit on the surface of the earth down the drill string and through ports provided in the drill bit to the well bottom and circulated back to the surface through the annulus formed about the drill string.

Drilling fluids are employed in the drilling system for a multitude of reasons including cooling and/or lubricating the drill bit and circulating the cuttings from the wellbore. Additionally, drilling fluids are utilized to maintain hydrostatic pressure on the subterranean formation through which the wellbore is drilled in order to prevent pressurized formation fluid from entering the wellbore.

Typically, wells are drilled into subterranean formations including sedimentary rock. Sedimentary rock in general has pores and can be permeable. In general, drilling fluid or drilling mud includes clay particles, fluid loss control agents and other additives in a liquid such as water or oil. In ordinary conditions, many of the clay particles are larger than the pores. When drilling mud contacts a newly created portion of a wellbore wall during drilling, the drilling fluid, driven by pressure differentials, will start to enter the pores in the wall. However, the larger clay particles that cannot enter the pores will together with the fluid loss control agents form a tight drilling fluid filter cake on the permeable wall to stop any clay particles from further entering the formation and to substantially slow down the liquid entering the formation. The amount of fluid lost into the formation before the tight drilling fluid filter cake on the wall is formed is commonly called "spurt loss," wherein the fluid may contain some fine clay particles and the liquid. After the drilling fluid filter cake is formed, the fluid lost to the formation through the cake is only the liquid.

Conventional drilling fluids have been designed to minimize the spurt loss and the fluid loss into porous formations by forming tight drilling fluid filter cakes. During normal drilling, almost all drilling fluid pumped down hole will be circulated back to surface and there is only a minimum amount of drilling fluid lost into formations. However, conventional designs still fail to stop drilling fluid losses when the pores are too large for any clay particles to plug. Typically, in such instances, no filter cake can form and the drilling fluid, including the clay particles and the liquid, will flow away from the wellbore into the formations rather than circulate back to surface. This is commonly referred to as "lost circulation" or "lost returns." Similarly, lost circulation may also happen when large open fractures or vugs are encountered during drilling. The wellbore interval where drilling fluid is lost is often referred to as a "lost circulation zone."

In addition, a wellbore may simply not be sufficiently competent to support the pressure applied by the drilling fluid and may break down under this pressure and allow the drilling fluid to flow away into the formation through generated fractures. This may occur when the wellbore integrity has been exceeded by the wellbore pressure. Such instances can occur when the weight of the drilling fluid provided creates a higher hydrostatic pressure than the wellbore can support. In such instances, the wellbore is not able to contain this much pressure and typically fractures, thereby allowing the drilling fluid to flow into the formation. The maximum pressure a wellbore can contain is referred to as wellbore pressure containment. When the wellbore pressure containment of a wellbore is improved, the wellbore is strengthened and behaves stronger. Therefore, improving wellbore pressure containment sometimes is referred to as wellbore strengthening.

The hydrostatic pressure in the well is in part determined by the weight (or density) of the drilling fluid used. The weight of the drilling fluid is important as it determines the hydrostatic pressure in the wellbore at any given depth, which prevents the formation fluid such as hydrocarbon or water from flowing into the wellbore and prevent a well blowout in extreme cases. Additionally, the weighted drilling fluid provides assistance in keeping the walls of the wellbore from collapsing while drilling. While the drilling fluid is circulating upward in the annulus in the wellbore, friction of the drilling fluid against the wellbore walls creates additional pressure to the wellbore. Thus, drilling operations often consider equivalent circulating density (ECD) of a drilling fluid, which is equivalent to the circulating friction pressure in the annulus, plus the static head of the fluid due to the density of the fluid.

Conventionally, a section of wellbore is drilled to the depth where the ECD creates a wellbore pressure approaching the wellbore integrity before action is taken to prevent fracturing. For example, intervals of the wellbore may contain weak or lost circulation formations above a permeable high pressure formation. In such an instance, a lower weight drilling fluid may be employed in the drilling process and steel casing strings of sequentially reducing diameters may be installed in the wellbore to protect the weaker zones above the permeable high pressure zone. Such casing strings are provided so that higher weight drilling fluid may be used in the permeable high pressure formation intervals without allowing for drilling fluid to fracture the weak or lost circulation formations. Stopping the drilling process to run casing in the well is very costly and time consuming. Additionally, each casing string added has a smaller diameter than the previous string, which may create impractical well dimensions depending on the number of casing strings needed to complete the well. In such cases, the reduced hole diameter created by the casing strings may create an impractical drilling situation. If a higher weight drilling fluid could be used in these weaker zones without the weaker zones being protected by steel casing, a well could be drilled into the higher and deeper high pressure zones with less casing. Elimination of one or more casing strings from a well can provide important savings in time, material and costs of drilling the well.

As mentioned above, drilling fluids can enter the formation through a fracture, either a pre-existing fracture or a fracture induced by the hydraulic pressure created in the wellbore during the drilling process. Commonly, drilling fluids employed are oil, synthetic or water based. These fluids are treated to provide desired rheological properties which make the fluids particularly useful in the drilling of wells. Generally, drilling fluid does not contain large particles capable of blocking and/or sealing the fractures and often fails to stop lost circulation. Intuitively, large particles, commonly referred to as Lost Circulation Material (LCM) sometimes are arbitrarily added to regular drilling fluid in attempt to plug fractures for preventing or curing lost circulation. Such particles added to the drilling fluid can include calcium carbonate, sand, coke, nut hulls, corn cobs, fiber, paper, ground paper, asphalt, wood chips, engineering plastics, pistachio hulls, almond hulls, peanut hulls, clay, and weighting materials such as barite and hematite. After being added with some larger particulates, a fluid may become a particulate fracture sealing fluid.

For at least the foregoing reasons including retaining the formation fluid in the formation and preventing the wellbore from collapsing, it is advantageous for a hydrocarbon well to contain high pressure in the wellbore during the drilling process. The ability of a wellbore to contain pressure is largely defined by the stress that holds the wellbore against being inflated and eventually fractured by wellbore pressure. In a subterranean formation, stresses naturally exist. Stresses in different formations can vary greatly in magnitude. Additionally, after a circular wellbore is created in a stressed formation, the stress field then is re-disturbed around the wellbore and a concentrated stress area is naturally formed. The undisturbed far-field stresses away from the wellbore may remain the same. The concentrated stress area is narrow and is proximate to the wellbore. The concentrated stress surrounding the wellbore gradually changes to the magnitude of the far field stresses within only two to three times the wellbore radius. For instance, if a wellbore is 4.25 inches in radius, the concentrated stress area will often dissipate in about 10 inches from the wellbore wall. This concentrated near-wellbore stress, sometimes referred to as "hoop stress", can be much larger than the far-field stresses. Though this stress concentration area is only around the wellbore, it can enable a wellbore to hold much higher pressure than without it. Due to the variation of stresses in different formations, some intervals of a wellbore may be capable of holding more pressure than others. In some cases, drilling operators have been unknowingly relying on this near-wellbore stress riser for containing higher wellbore pressure.

Generally, drilling operations can be conducted in many different rock formations. Some rock can be very brittle. Under tectonic stresses, many rock formations are fractured. When the surfaces of these fractures are mismatched or there is debris inside the fractures, the fractures may not close properly even under high formation stresses and may leak or be hydraulically conductive to the drilling fluid. Typically, it does not require a long leaking fracture to connect a wellbore to its far field low stress environment and cause wellbore fluid to bypass this narrow near-wellbore stress concentration region. Generally, when this occurs, the high hoop stress can no longer help the wellbore to hold higher pressure any more. How much pressure a wellbore interval can contain is defined by the weakest formation. Only one leaking fracture penetrating a wellbore can substantially lower the pressure containment for the entire wellbore interval.

Furthermore, even when a leaking fracture is very short, such as only 0.1 inch long or a small crack, studies (Wang, et al., "Fractured Wellbore Stress Analysis: Sealing Cracks to Strengthen a Wellbore," SPE/IADC (Society of Petroleum Engineers/International Association of Drilling Contractors) 104947, published at the 2007 SPE/IADC Drilling Conference held in Amsterdam, The Netherlands, 20-22 Feb. 2007) show it can still substantially lower the wellbore pressure containment. Such a crack can be easily extended further at a pressure much lower than the near wellbore stress to connect to the low far-field stress region. Similarly, other flaws such as notches caused by drill bits may also lower the pressure required to induce a fracture.

When there is a large stress concentration around a wellbore, studies (Wang, et al., "Fractured Wellbore Stress Analysis: Sealing Cracks to Strengthen a Wellbore," SPE/IADC (Society of Petroleum Engineers/International Association of Drilling Contractors) 104947, published at the 2007 SPE/IADC Drilling Conference held in Amsterdam, The Netherlands, 20-22 Feb. 2007) have shown that sealing these leaking fractures can substantially improve wellbore pressure containment. Sealing leaking fractures can put the otherwise bypassed higher near wellbore stresses into use to help the wellbore to hold much higher pressure than the lower undisturbed far field stresses alone can. Sealing leaking fractures can strengthen a wellbore even substantially beyond what its natural hoop stress can provide. When sealing fractures for a higher wellbore strength or wellbore pressure containment is achieved by a fracture sealing fluid, such a sealing fluid is referred to as a wellbore strengthening fluid.

There are known methods in the art related to the sealing of the fracture and the inherent strengthening of the wellbore thereby. In one conventional method, particulates are added to drilling fluid in an attempt to seal off a lost circulation zone to stop lost circulation. For example, in a conventional method, particulates are arbitrarily added to drilling fluid to seal fractures. However, arbitrary particulates or particulates defined based on an empirical equation added to drilling fluid to seal off fractures are typically inefficient and unreliable due to lack of knowledge regarding certain fracture properties, including fracture width, especially after some fluid has invaded into the fracture.

When there is not enough hoop stress around the wellbore, simply sealing a fracture can not strengthen a wellbore. In this case, in another conventional method of strengthening the wellbore when there is not enough stress concentration around a wellbore, a fracture is purposely induced and propped and sustained to increase the hoop stress of the wellbore correspondingly. Based on its established fracture propping model, needed increase in wellbore strength equals the induced additional hoop stress, which is correlated to a certain propped fracture width. This width and induced stress is to be sustained by fracture propping particulates matching the fracture width. Based on this fracture width sustaining model, the number of the propping particulates in drilling fluid matching the size of the needed fracture width is calculated. The concentration of a particulate composition is then calculated based on the percentage of the propping particulates in the particulate composition.

In the above mentioned method, apparently too large of particulates can not be forced into small fractures and too small of particulates do not have enough propping functions. This method requires an accurate determination of the required fracture width and prefers particulates matching the desired fracture propping width.

The data provided in the directly aforementioned conventional method is unlikely to be available and completely accurate at all times. For example, when an unknown fracture length is estimated, it results in the predicted fracture width also being estimated. Such an estimate can skew the data on which the models are based, which in turn affects the predicted fracture width. The skewed data can be problematic in that the optimal size of the propping particulates for inducing and maintaining the increased hoop stress is based on the predicted fracture width. If the fracture width in fact is much larger than predicted, the propping particulates may not stay inside the fracture mouth and may not induce enough hoop stress. If the fracture width is much smaller than predicted, the propping particulates may not be able to enter the fracture for the propping effect and no additional hoop stress can be induced. Moreover, if the fracture width after the particulate composition is circulated is determined to be different from the previously predicted fracture width, typically the particulate composition has to be changed to remain optimized. However, changing the particulate composition at a rig site can have enormous logistical and cost issues and is generally avoided since each job may call for an amount of 150,000 to 500,000 pounds of such particulates.

For any case, in the above mentioned method, the needed fracture width is determined after all the data are defined. It is therefore unpractical to define an optimized propping composition before the fracture width is defined. Every case will therefore require an optimized composition to be customized and that it is impossible to for a composition to be made ready ahead of time results in a low efficiency.

Furthermore, during drilling a large quantity of drilled cuttings are generated and carried back by the circulated drilling fluid. At the surface, solid control systems such as shale shakers with screens are used to separate and dispose of the cuttings from the drilling fluid to keep the needed properties from deteriorating. However, when particulates are added into the drilling fluid, these cuttings are mixed with the added particulates. In order to keep the added particulates in the drilling fluid, the mesh size of the screens has to be designed to ensure the added particulates can pass through so that it will not be discarded together with the drilled cuttings and lower the performance of the designed particulate fluid. If the particulate size of the particulate fluid is changed, the mesh screen may have to be changed in order to properly screen out the cuttings, while retaining the particulates. Such screen mesh sizes may be unavailable, as there are only a few mesh sizes commercially available. If the mesh size is inadequate for the particulate size distribution, the composition of the particulate fluid will be compromised and unlikely to provide the intended benefits.

Still further, in the conventional method wherein a fracture propping composition for inducing additional hoop stress is designed based on a derived fracture width based on other well conditions such as an estimated fracture length, there is no appropriate criterion for quantifying its propping performance with a lab test for the derived fracture width. Without such a criterion, quality control for a fracture propping composition cannot be meaningfully implemented. Particulates normally are manufactured out of such as hammer mills. Due to the unevenness of the raw materials and the processing method, the particulates manufactured tend to vary much from batch to batch. A lab test is important for quality controlling a formulated particulate fluid on its needed function.

In view of the above, a need still exists for an inexpensive and time-efficient flexible method to implement at a rig site to substantially strengthen a portion of a wellbore of a hydrocarbon well. It would be further desirable to transform well bore fluid to include particulates of a suitable size and quantity to reinforce a fractured zone of a well bore utilizing pumps, hoppers, blenders and well fluid holding tanks. It would further be desirable to substantially strengthen a wellbore utilizing a minimal amount of hardware and machinery, such that transport cost and time to the well site would be minimized. It would still further be desirable to strengthen a wellbore utilizing a method that does not require accurate data. It would also be desirable to utilize a particulate fluid, wherein many characteristics of the particulate fluid would remain constant throughout the strengthening process. Additionally, it would be desirable to employ a wellbore strengthening method of substantially sealing off a fracture, wherein the propping of the fracture is unnecessary. Furthermore, it would be desirable to employ a method of substantially sealing off a fracture and the wellbore such that the wellbore could contain a higher pressure therein.

SUMMARY

Upon entering a fracture, a drilling fluid driven by wellbore pressure can inflate the fracture wider and propagate the fracture longer. Generally, if drilling fluid is continuously supplied to the fracture, the fracture will grow longer and wider. This process is known as hydraulic fracturing. Hydraulic fractures are inflated by fluid invasion and propped open by hydraulic pressure of the fluid against formation stresses. The fracture width of a hydraulic fracture is related to the volume of the invasion fluid. In a particulate fracture sealing fluid, particulates are suspended in fluid and carried to fractures by the fluid. When particulates arrive at the entrance of a fracture, there has been some fluid flowing into the fracture and widening the fracture to be sealed. A fluid with particulates large enough to plug the initial fracture width may not be able to plug the fracture widened by the invasion fluid into the fracture ahead of the particulates.

Hydraulic fracturing is controlled by fluid invasion. A fast invasion can propagate a fracture fast and a slow invasion can propagate a fracture slowly. During a fracturing process, if the supply of the invasion fluid is suddenly cut off, the fracture can then no longer grow wider and the fracture propagation is arrested. For a weak wellbore, fluid is lost into formations by fracturing. As long as the fluid supply into the fracture is cut off and fracture propagation is arrested, wellbore fluid is contained and no lost circulation can occur. Cutting off the fluid supply into a fracture can be achieved by sealing the fracture with particulates mixed in a fluid.

If a particulate fracture sealing fluid formed an effective seal as soon as the sealing fluid entered the fracture, the fracture would increase minimally in width and length. Particulate-treated mud contains particulates suspended in a liquid such as oil or water. Even smaller particles, such as barite and clay, may also be present. Particulate sealing is achieved by accumulation of particulates, preferably, of different sizes. This accumulation process actually is filtration against a fracture mouth or a tight spot inside a fracture. However, at the fracture mouth, there is a sudden geometry change and therefore this location is most reliable for particulates to block a fracture as long as the particulate are larger than the width at the fracture mouth. When a fracture is encountered during drilling, particulates are carried to a fracture by the liquid. During the process of fluid flowing into a crack or a small fracture, some liquid and smaller particles can directly pass the fracture mouth or the entrance and flow into the fracture. However, those particulates larger than the fracture mouth may soon block the fracture mouth. When this occurs, the flow into the fracture is restricted and can only enter the gaps between these large particulates. Further flow into the fracture can carry some small particulates to block these gaps. Eventually, the gaps between the large and small particulates are small enough that the colloidal size clay particles in the mud can form a layer of a tight mud cake. As with any filtration process, before forming this mud cake or a tight seal, the flow is in an uncontrolled manner, and the fluid flowing into the fracture contains many different particles. This portion of the fluid is called a spurt loss. After forming the mud cake, the flow is well-controlled and only filtrate or clear liquid can slowly pass through the formed tight seal. There is always some spurt loss fluid entering a fracture before the particulates seal the fracture. When more particulates are added to the mud, the accumulation of sealing particulates can be realized sooner, and the spurt loss volume tends to be smaller. The spurt loss fluid entering the fracture before the seal formed will inflate the fracture to a fracture width corresponding to the invaded spurt loss volume. More fluid entering can inflate the fracture wider. During fluid invasion, a fracture can continuously increase in width. However, a particulate sealing fluid can not seal a fracture wider than the sealing particulates can seal. A particulate sealing composition can be designed to seal up to only a certain fracture width not any wider. This fracture width can be called as a critical sealing width. This width is determined primarily by the size of the large particulates and is a characteristic of a particulate sealing fluid. During a hydraulic fracturing process, the volume of the invasion fluid required to open the fracture to the critical sealing width is referred to as a fracture volume capacity. Therefore, in order to securely form the particulate seal, it is important that the spurt loss volume of the sealing fluid is equal to or smaller than the fracture volume capacity.

After a fracture is securely sealed, the trapped pressure inside the fracture can be bled off through the formation pores or by extending the fracture tip further. After the fracture is sealed, the wellbore flaw is fixed and the wellbore is strengthened.

An embodiment of the present invention is a method for substantially sealing at least a portion of a wall of a wellbore of a well penetrating a formation. The method includes selecting a fracture sealing width at a sealing location of a fracture to be sealed defined by the portion of the wellbore wall and the formation. The fracture includes a fracture mouth proximate to and defined by the portion of the wellbore wall, and a fracture tip defined by the formation and distal to the fracture mouth. The fracture also includes a fracture length, wherein the fracture length is the distance from the fracture mouth to the fracture tip. The sealing location can be the fracture mouth or any where along the fracture. In an embodiment, a fracture seal is formed at the fracture mouth inside the wellbore. In an embodiment, a fracture seal is formed proximate to the fracture mouth. In an embodiment, a fracture seal is formed inside the fracture.

A fracture sealing width at a sealing location can be arbitrarily selected, however, to make the method more practical and economical, it can be selected based on an evaluation with some other factors such as fracture length, wellbore radius, flow restrictions, tools, possible mechanical interference to moving parts of a tool, pressure, strengthening effects, formation mechanical properties, deviation, temperature, stress, sealing particulates, fluid for using the sealing particulates in and/or shale shaker screens. In an embodiment, a fracture sealing width is selected independently upon fracture length.

The method also includes formulating a fracture sealing composition of a sealing fluid at least based on the selected fracture sealing width. The sealing fluid includes drilling fluid and a concentration of one or more particulates forming the fracture sealing composition. The method further includes determining or defining a spurt loss volume of the sealing fluid based at least on the fracture sealing width, determining a fracture volume capacity of the fracture based at least on the fracture sealing width, and comparing the spurt loss volume of the sealing fluid to the fracture volume capacity. If the sealing fluid has a spurt loss volume less than or equal to the fracture volume capacity, the sealing composition (particulates of different sizes defined in a mixing ratio) can be manufactured in bulk quantities, e.g., 250,000 pounds and transported to the site of the drill rig and mixed with fluid. The mixing may utilize hoppers or blenders in communication with holding tanks. This is part of the fluid circulating system that pumps fluid and particles downhole to the drill bit and returned through the annulus between the wellbore and drill string. The manufacturing may utilize crushers or shredders such as a hammer mill, sizing screens, scales, conveyors and baggers. The sealing fluid is circulated in the wellbore, wherein the sealing fluid forms a sealing relationship with the fracture, thereby substantially sealing at least the portion of the wall of the wellbore. The sealing fluid can form a sealing relationship with the fracture proximate to the fracture mouth.

The method can also include modifying the concentration of the fracture sealing composition of the sealing fluid where the sealing fluid has a spurt loss volume greater than the fracture volume capacity, whereby the modified sealing fluid (having the modified sealing fluid composition) comprises a spurt loss volume less than or equal to the fracture volume capacity. Typically the modification entails adding additional composition to the fluid to increase particle concentration. In one embodiment, additional particulates are added to the fluid to reduce the spurt loss volume.

The fracture sealing width can be selected independently of a parameter selected from the group consisting of the fracture length, a selected sealing location along the fracture, a Poisson's ratio of the formation, a Young's modulus of the formation, a distance from the center of the wellbore to the fracture tip, a net pressure keeping the fracture open, and combinations thereof. The fracture sealing width can include a summation of an initial fracture width and an additional fracture growth width. Optionally, the initial fracture width of the fracture is substantially zero. Optionally, the selected fracture sealing width is held constant throughout the method.

The net pressure that keeps the fracture open is the fluid pressure inside the fracture greater than the formation stress. The formation stress tends to close the fracture. The fluid pressure inside the fracture or the fracture pressure can be as high as the wellbore pressure. In an embodiment, the fluid pressure inside the fracture equals the wellbore pressure. The formation stress that tends to close the fracture can be as low as the least principal stress in the formation. In an embodiment, the formation stress that tends to close the fracture is the least principal stress in the formation. The least principal stress in the formation often is the minimum horizontal stress of the formation that defines the fracture gradient. In an embodiment, the net pressure is the wellbore pressure less the minimum horizontal stress.

The fracture volume capacity is the volume of fluid the fracture is capable of containing when the fracture is inflated to the fracture sealing width at the sealing location such as a fracture mouth under downhole conditions. The fracture volume capacity can be evaluated by analytical methods; numerical methods such as boundary element analysis, discrete element analysis, finite difference analysis and finite element analysis; or computer simulations. Optionally, the fracture volume capacity is determined by calculating a parameter L by:

$$L = \sqrt{\left(\frac{W(R) \cdot E}{4(1-v^2)\Delta P}\right)^2 + R^2}$$

wherein W(R) is the selected fracture sealing width at the fracture mouth, ν defines a Poisson's ratio of the formation, R is the wellbore radius, E defines a Young's modulus of the formation, ν defines a Poisson's ratio of the formation, the parameter L defines the distance from the center of the wellbore to the fracture tip, and ΔP defines a net pressure in the fracture that keeps the fracture open. A pressurized fracture cross section area, A, from the fracture mouth to the fracture tip L is calculated by:

$$A = \int_R^L W(x) dx$$

wherein W(x) is an inflated fracture width at a location x between the fracture mouth and the fracture tip location defined by the parameter L along the fracture as a function of the location x and is defined by:

$$W(x) = \frac{4(1-v^2)\Delta P}{E}\sqrt{L^2 - x^2}$$

and the fracture volume capacity $V_c$ is calculated by:

$$V_c = A \cdot H$$

wherein H defines a fracture height.

The spurt loss volume is defined as the volume of a particulate sealing fluid flowing through a sealing location such as a fracture mouth before a seal that only allows filtrate to pass has formed. During this flowing through process, this spurt loss volume is propagating the fracture and inflating the fracture to a fracture width. This spurt loss volume has no direct relationship with a portion of the particulate composition in a sealing fluid. This spurt loss volume is a result of the particulate packing efficiency of all large, medium and small particulates. The packing efficiency is affected by the shape, size, size distribution, compressibility, surface charge, surface roughness, strength, elasticity, plasticity, ratio, etc. of all particles in the sealing fluid. It can be further affected by temperature and pressure. Due to complexity, it is impossible to reliably calculate the spurt loss based on a portion or all of the particulates without being aided by lab tests. However, this spurt loss volume can be easily defined by lab tests, which simulate this sealing through process. Furthermore, this spurt loss volume can be measured by simple lab tests. The spurt loss volume of the sealing fluid can be measured in part by flowing the sealing fluid through a filtration medium opening defined in a filtration medium, wherein if the spurt loss volume of the sealing fluid is less than or equal to the fracture volume capacity, the sealing fluid can be transported to the wellbore. Optionally, the spurt loss volume is further measured by utilizing a fluid loss test cell. The fluid loss test cell can be a permeability plugging apparatus test cell, and the equivalent spurt loss volume can be further measured in accordance with API Recommended Practice 13I. The filtration medium opening can be a slot defined by the filtration medium, wherein the filtration medium can be a slot disk. The slot defined by the slot disk can include a slot length and a slot width, wherein the slot width can be equivalent to the fracture sealing width. Optionally, the filtration medium can have a flow path similar to a fracture with the width at the entrance equivalent to the select fracture sealing width.

Optionally, the spurt loss volume is defined by a unit slot length spurt loss volume, wherein the unit slot length spurt loss volume of the sealing fluid is determined by dividing the measured spurt loss volume by the slot length of a slot disk. The method can further include determining a unit height fracture volume capacity from the fracture volume capacity and the fracture height. Optionally, if the unit slot length spurt loss volume of the sealing fluid is less than or equal to the unit height fracture volume capacity, the sealing composition can be manufactured in bulk quantities and transported to the wellbore.

It is beneficial to measure the spurt loss volumes of a sealing composition in a base fluid at different concentrations to predetermine the relationship between the spurt loss volume and the concentration. Therefore, in one embodiment, the concentration of a sealing composition is determined based on a predetermined relationship between the spurt loss volume and the concentration of the sealing composition. At the time of applications, when the required spurt loss volume is determined, a needed concentration of the composition can be immediately determined without doing further lab tests. Aided with lab tests, it is also beneficial to derive mathematical equations to describe such a relationship for a sealing composition so that a needed concentration of the sealing composition can be calculated based on computer simulation after the needed spurt loss is defined based on the calculated fracture volume capacity. In this case, a spurt loss process for such a sealing composition can be simulated with a special computer program. Furthermore, combined with a computer simulated hydraulic fracturing process, the spurt loss process can be integrated into the fracturing process to determine the needed concentration for the sealing composition. In one embodiment, the concentration of a sealing composition is determined by a computer simulated spurt loss process. In another embodiment, the concentration of the sealing composition is determined by a computer program simulating the spurt loss process during hydraulic fracturing. Optional, after the concentration of the sealing composition is determined with the calculations or simulations, the spurt loss volume is further verified by a lab test in one embodiment.

The relationship between a particle size distribution of the fracture sealing composition and the fracture sealing width can remain substantially constant throughout the method after the formulation of the fracture sealing composition. Optionally, the concentration of the fracture sealing composition in the sealing fluid is varied to ensure that the relationship between the particle size distribution of the fracture sealing composition and the fracture sealing width remains substantially constant throughout the method after the formulation of the fracture sealing composition.

Optionally, at least a portion of at least one particulate of the one or more particulates is smaller than the selected fracture sealing width. Optionally at least a port of at least one particulate of the one or more particulates is larger than the selected fracture sealing width. Optionally, the volume of the particulates that have at least one dimension 100 to 150 percent of a selected fracture sealing width is 5 to 35 percent of the total volume of all the sealing particulates in a sealing composition. The one or more particulates can be selected from the group consisting of calcium carbonate, sand, coke, petroleum coke, graphite, resilient graphitic carbon, synthetic graphite, cedar fiber, nut hulls, corn cobs, fiber, synthetic fiber, paper, threaded paper, ground paper, carbon fiber, threaded rug, asphalt, gilsonite, rubber, foam rubber, drilled cuttings, saw dust, mica, wood chips, engineering plastics, hollow spheres, fly ash, hollow plastic spheres, hollow glass spheres, cotton seed hulls, walnut hulls, pistachio hulls, almond hulls, peanut hulls, cement, clay, bentonite, modified clay, organoclay, limestone, dolomite, marble, resin particles, metal particles, ceramic particles, nanotechnology particles, weighting materials such as barite, hematite, iron oxide, ilmenite, and combinations thereof.

In another embodiment, a method is provided for sealing at least one fracture defined by a portion of a wall of a wellbore of a well and a formation through which the well penetrates. The method includes formulating a fracture sealing composition of a sealing fluid including a base fluid or wellbore fluid such as a drilling fluid, a cementing fluid, a spacer fluid, a completion fluid, a drill-in fluid, a workover fluid, water, brine, oil, diesel or synthetic oil and a concentration of one or more particulates forming the fracture sealing composition. The fracture sealing composition of the sealing fluid is at least based on a selected fracture sealing width of the fracture. The fracture includes a fracture mouth proximate to and defined by the portion of the wellbore wall, and a fracture tip defined by the formation and distal to the fracture mouth. The fracture further includes a fracture length, wherein the fracture length is the distance from the fracture mouth to the fracture tip. Optionally, the fracture sealing width is selected independently of at least the fracture length. The fracture sealing composition of the sealing fluid is also based on a fracture volume capacity based at least on the fracture sealing width.

The method further includes circulating the sealing fluid in the wellbore, wherein the circulating sealing fluid forms a sealing relationship with the fracture and the sealing relationship is formed proximate to the fracture mouth.

The method further includes transporting the sealing fluid to a fracture in a wellbore, wherein the sealing fluid forms a sealing relationship with the fracture and sealing relationship is formed proximate to the fracture mouth, pressurizing the wellbore gradually to ensure the sealing has been achieved.

In yet another embodiment, a method is provided for sealing at least a portion of a wellbore wall of a well penetrating a formation. The method includes selecting a fracture sealing width of a fracture defined by the portion of the wellbore wall and the formation. The selected fracture sealing width is held constant throughout the method and the fracture sealing width is selected independently of at least a corresponding fracture length of the fracture. The method also includes formulating a sealing fluid including a wellbore fluid and a concentration of one or more particulates forming a fracture sealing composition. At least a portion of at least one particulate of the one or more particulates is larger than the selected fracture sealing width of the fracture.

The method further includes determining a spurt loss volume of the sealing fluid. The spurt loss volume is measured in part by utilizing a fluid loss test cell, wherein the sealing fluid under a pre-determined pressure is passed through a filtration medium opening defined by a filtration medium. The filtration medium opening includes a filtration medium opening length and a filtration medium opening width. The filtration medium opening is sized and configured such that the filtration medium opening length is larger than the filtration medium opening width. The filtration medium opening is sized and configured to mimic a fracture entrance. Optionally, the filtration medium opening is sized and configured to mimic a fracture.

The method also includes comparing the spurt loss volume of the sealing fluid to a fracture volume capacity. The method also includes modifying the concentration of the one or more particulates of the fracture sealing composition of the sealing fluid if the spurt loss volume of the sealing fluid is greater than the fracture volume capacity. The sealing fluid having the modified concentration of the one or more particulates of the fracture sealing composition includes a modified spurt loss volume less than or equal to the fracture volume capacity. The sealing fluid is circulated to the wellbore, wherein the circulating sealing fluid forms a sealing relationship with the fracture.

The method also includes determining a fracture volume capacity based on a selected fracture sealing width and modifying the particulate composition in a fracture sealing fluid so that the spurt loss volume of the sealing fluid is less or equal to the fracture volume capacity. The fracture sealing fluid is pumped to the wellbore.

The base fluid for the fracture sealing fluid includes any wellbore fluid such as drilling fluid, mud, oil based mud, synthetic based mud, water based mud, completion fluid, cementing slurry, spacer fluid, drill-in fluid or workover fluid, water, brine, oil, diesel or synthetic oil.

Other possible embodiments include two or more of the above embodiments of the invention. In an embodiment the method includes all of the above embodiments and the various procedures can be carried out in any order.

DETAILED DESCRIPTION

Figure 1:
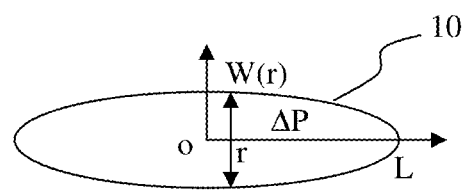
FIG. 1 illustrates a line crack of an elliptical shape consistent with an embodiment of the present invention.

The present invention is related to a method of improving pressure containment of a wellbore of a well during engineering operations of a well for hydrocarbons utilizing a wellbore strengthening fluid. In an embodiment, the method includes selecting a fracture sealing width; selecting a particulate fracture sealing fluid; determining a spurt loss volume and a fracture volume capacity; confirming that the spurt loss volume is equal to or less than the fracture volume capacity; and formulating the particulate size and concentration and mixing a production quantity of the wellbore strengthening fluid, pumping the wellbore strengthening fluid downhole, wherein a fracture in the wellbore is sealed. In an alternate embodiment, the method includes confirming that the spurt loss volume of the particulate fracture sealing fluid is less than or equal to the fracture volume capacity. In yet another embodiment, the method further includes calculating a unit slot length spurt loss volume and an unit height fracture volume capacity, wherein the unit slot length spurt loss volume is less than or equal to the unit height fracture volume capacity. The aforementioned embodiments and other embodiments will be discussed in more detail below in addition to the Figures included herein.

In an embodiment of the present invention, a method is provided for sealing at least one fracture in a wellbore wall, thereby strengthening the wellbore and improving the wellbore pressure containment. Specifically, a method in one embodiment is provided for improving wellbore pressure containment during the drilling of the well. The fracture to be sealed can be a natural fracture or an induced fracture. More specifically, the fracture to be sealed can be a fracture induced in a present drilling process, a pre-existing fracture, a natural fracture, a closed fracture, a leaking fracture, a hydraulically conductive fracture, an inflated fracture or an open fracture. Optionally, a plurality of fractures in a wellbore wall can be sealed. In an embodiment wherein a plurality of fractures can be sealed, an exemplary method will provide for the sealing of the fracture having the least fracture volume capacity of the plurality of fractures, thereby providing for the sealing of any fractures larger than the least fracture volume capacity. Such a method will be discussed in further detail below.

The fracture in the wellbore wall can be sealed by a sealing fluid. In at least one embodiment, the sealing fluid is a particulate fracture sealing fluid including a base fluid such as a drilling fluid, a cementing fluid, a spacer fluid, a completion fluid, a drill-in fluid or a workover fluid and a concentration of one or more particulates forming a fracture sealing composition. As discussed above, drilling fluid charged by wellbore pressure can enter an existing fracture and further inflate and propagate the fracture. Optionally, the drilling fluid may induce a fracture. If the drilling fluid is being continuously forced in, the fracture may further propagate at a rate/distance at least in part dependent on the physical characteristics of the formation, e.g., permeability and/or modulus of the rock formation. However, if the supply of drilling fluid into the fracture is terminated by a manner such as a seal, the fracture propagation can be arrested. The circulation of drilling fluid may be sustainable without substantial losses of drilling fluid into the fracture in the wellbore when the fracture propagation ceases. Thus, a method is provided in at least one embodiment of the present invention for circulating a sealing fluid having sufficient properties in the wellbore to seal the fracture. In an embodiment, a method is provided for determining the particulate fracture sealing fluid required to substantially seal the fracture in the wellbore wall. In an exemplary embodiment, the relationship between a particle size distribution of the fracture sealing composition and a fracture sealing width remains substantially constant throughout the method after the formulation of the fracture sealing composition. The concentration of the fracture sealing composition in the sealing fluid can be varied to ensure that the relationship between the particle size distribution of the fracture sealing composition and the fracture sealing width remains substantially constant throughout the method after the formulation of the fracture sealing composition. The concentration of the fracture sealing composition can also be varied to ensure that the relationship between the particle size distribution of the fracture sealing composition and the fracture sealing width remains substantially constant in a changed wellbore condition.

A fracture sealing width can be selected to favor the sealing or other engineering operations by evaluating many factors. Accordingly, in an exemplary embodiment, a fracture sealing width is selected to assist in determining an optimized fracture sealing composition to be utilized in sealing the fracture, wherein the selected fracture sealing width remains constant such that the selected fracture sealing width does not change during the process of sealing the fracture and thereby strengthening the wellbore of the well. If a particulate fracture sealing fluid formed an effective seal as soon as the sealing fluid entered a fracture, the propagation of the fracture in width and length would be minimal and an initial fracture width of the fracture could be used as the fracture sealing width. However, particulates are suspended in the particulate fracture sealing fluid, and it is normal to have some of the fluid portion of the particulate fracture sealing fluid flowing ahead of the sealing particulates and into the fracture before the particulates form an effective seal. The particulate fracture sealing fluid entering the fracture before the seal formed can inflate the fracture to a fracture width corresponding to the invaded fluid volume. This fracture width is referred to as an inflated fracture width. More particulate fracture sealing fluid invading the fracture can inflate the fracture wider. During particulate fracture sealing fluid invasion, the fracture can be continuously increasing its width. Thus, such expansion in the width of the fracture must be taken into account when selecting the fracture sealing width. Thus, in one embodiment of the present invention, the fracture sealing width is the inflated fracture width wherein the inflated fracture width is the total fracture width of the fracture after expansion by the invasion of particulate sealing fluid.

Figure 7:
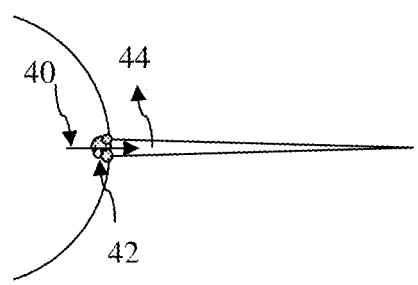
FIG. 7 illustrates a top plan view of a wellbore wherein a particulate seal formed inside the wellbore at the fracture mouth of a fracture by a particulate sealing fluid flowing into the fracture, as shown consistent with an embodiment of the present invention.

An embodiment of the present invention is a method for substantially sealing at least a portion of a wall of a wellbore of a well penetrating a formation. The method includes selecting a fracture sealing width at a sealing location of a fracture to be sealed defined by the portion of the wellbore wall and the formation. The fracture includes a fracture mouth proximate to and defined by the portion of the wellbore wall, and a fracture tip defined by the formation and distal to the fracture mouth. The fracture also includes a fracture length, wherein the fracture length is the distance from the fracture mouth to the fracture tip. The sealing location can be the fracture mouth or any where along the fracture. However, for a more reliable seal and more strengthening effect, it is preferable to seal at the fracture mouth as shown in FIG. 7. In FIG. 7, when particulate sealing fluid flows into a fracture 44 defined by the wall of the wellbore and the formation along a flow direction 40, a particulate seal 42 can be formed by filtration against the fracture mouth. In an embodiment, a fracture seal is formed at the fracture mouth inside the wellbore. In an embodiment, a fracture seal is formed proximate to the fracture mouth. In an embodiment, a fracture seal is formed inside the fracture.

In an alternate embodiment, the fracture sealing width is the summation of the initial fracture width and the estimated fracture growth width, wherein the estimated fracture growth width includes the expansion of the fracture width from the initial fracture width caused by the invasion of particulate sealing fluid. In another embodiment, the fracture sealing width is determined based on an estimate of the fracture length. The fracture length can be defined as the distance from the fracture mouth to the fracture tip. For an existing natural fracture, only the inflated portion of the fracture is considered when determining a fracture length. Still yet, in another embodiment, the fracture sealing width is selected based on the preferred screen size of the shale shaker so that the selected sealing particulates in a sealing fluid can pass the screen without being discarded together with the larger drilled cuttings in the sealing fluid during a solid control process.

Additionally, one of ordinary skill in the art will appreciate that a conventional location for sealing the fracture includes the fracture mouth, wherein the term "fracture mouth" refers to the fracture opening at the wellbore wall location. It is understood that sealing at other fracture locations such as inside the fracture away from the fracture mouth can also strengthen the wellbore; however such fracture locations generally strengthen the wellbore less than sealing at the fracture mouth for the same efforts. Thus, in an exemplary embodiment, the fracture sealing width is based on the fracture width at a location proximate to the fracture mouth and the fracture is sealed proximate to the fracture mouth.

Limited by the largest particulate size in a fracture sealing fluid, the particulate fracture sealing fluid can only seal a fracture up to a certain fracture sealing width that the particulate fracture sealing fluid is designed to seal. However, such a fracture sealing fluid can seal fractures narrower than the fracture sealing width. Thus, for a particulate fracture sealing fluid designed to seal up to the fracture sealing width, the sealing fluid must form the seal before the fracture width grows to be wider than the fracture sealing width, otherwise the sealing fluid can no longer seal the fracture. This requires that the seal must form before the fluid invading the fracture inflates the fracture to a width wider than the selected fracture sealing width.

For a hydraulic fracture of a wellbore, there is a relationship between the fracture sealing width and the fluid volume entering the fracture. In an embodiment wherein the fracture sealing width, w, cannot be exceeded, a fluid volume invading the fracture to inflate it to the fracture sealing width, w, cannot be exceeded. This volume can be referred to as the fracture volume capacity, $V_c$, for the fracture. This is a characteristic of the fracture.

For a particulate fracture sealing fluid, a seal can be formed at a sealing location by accumulation of particulates against a flow restriction such as a fracture mouth. During the fluid invasion, in order to form the seal by accumulation, a portion of the sealing fluid flowing by the sealing location or the flow restriction is necessary. This necessary fluid volume flowing by the sealing location, referred to as spurt loss volume or $V_{sp}$, in order to form the needed seal is a characteristic of the particulate fracture sealing fluid.

In an exemplary embodiment, the spurt loss volume, $V_{sp}$, of a particulate fracture sealing fluid cannot exceed the fracture volume capacity, $V_c$, for the sealing fluid to seal a fracture. Accordingly, if $V_{sp}$ does not exceed $V_c$, the fracture will not inflate wider than the fracture sealing width and the particulate fracture sealing fluid can form the seal. However, if $V_{sp}$ exceeds $V_c$, the fracture will inflate wider than the fracture sealing width and this wider width exceeds the sealing capabilities of the designed particulate fracture sealing fluid. In this case, a fracture seal may not form with the sealing fluid.

The fracture volume capacity, $V_c$, can be defined or evaluated by different methods. In an embodiment, the fracture volume capacity, $V_c$, is defined by an analytical method. In an embodiment of an analytical method, the fracture mouth width is selected as the fracture sealing width to be sealed by a particulate fracture sealing fluid, wherein the fracture has no fluid leak-off (which will be discussed in further detail below). The fracture volume capacity for the fracture sealing width, which in this embodiment is the fracture mouth width, is calculated as follows below.

For a line crack or fracture 10 of an elliptical shape in a formation as shown in FIG. 1, the distance L from the fracture center defined as the origin O to the fracture tip, when the fluid pressure inflated fracture width at location r along the fracture is defined as W(r), has been defined as:

$$L = \sqrt{\left(\frac{W(r) \cdot E}{4(1-v^2)\Delta P}\right)^2 + r^2}$$ (Equation 1)

In the equation in this embodiment, v is the Poisson's ratio of the formation, E is the Young's modulus of the formation, L is the distance from the wellbore center to the fracture tip, and $\Delta P$ is the net pressure in the fracture that keeps the fracture open. The formation Poisson's ratio and Young's modulus are formation properties and can be viewed as constants. These formation properties can be obtained by lab tests on rock core samples.

Figure 2:
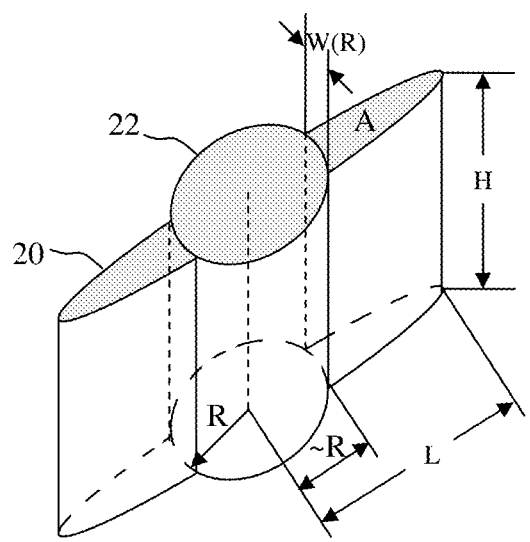
FIG. 2 illustrates a perspective view of a hydraulic fracture intercepted by a wellbore in the center of the fracture consistent with an embodiment of the present invention.

Alternatively, a cross section of a wellbore with a fracture can be viewed as a line crack being intercepted in the center by a circular wellbore with a radius R as shown in FIG. 2. In an embodiment wherein the fracture sealing width at the fracture mouth to be sealed is selected to be W(R), the distance L from the wellbore center to the fracture tip can be approximated as follows:

$$L = \sqrt{\left(\frac{W(R) \cdot E}{4(1-v^2)\Delta P}\right)^2 + R^2}$$ (Equation 2)

In FIG. 2, a three-dimensional illustration models a hydraulic fracture 20 intercepted by a wellbore 22 having a center defined as the origin O. As shown in the Figure, the following variables from Equation 2, 4 and 5 are: the fracture cross sectional area from mouth to tip A; the fracture height H; the distance L from the center of the wellbore to the fracture tip; the wellbore radius R; and the fracture sealing width at the fracture mouth W(R). As shown below, the fracture volume capacity, $V_c$, can be calculated from these variables by multiplying the fracture cross section area (A) from the fracture mouth to the fracture tip by the fracture height (H). If the height is known, the fracture volume capacity may be calculated once A is known, as shown below.

In an embodiment wherein the distance, L, is defined as the distance from the center of the wellbore, or the origin O to the fracture tip, Equation 2 can be manipulated as shown below in Equation 3 to determine the fracture width, W(x), as a function of its location x along the fracture.

$$W(x) = \frac{4(1-v^2)\Delta P}{E}\sqrt{L^2 - x^2}$$ (Equation 3)

In an embodiment, the pressurized fracture cross section area, A, from the wellbore wall to the fracture tip can be approximated by integrating the fracture width along the length of the pressurized fracture from the wellbore wall location, R, to the fracture tip location, L, as shown below.

$$A = \int_R^L W(x)dx$$ (Equation 4)

Accordingly, in an embodiment wherein the fracture height is H, the fracture volume capacity, $V_c$, can be determined as shown below.

$$V_c = A \cdot H$$ (Equation 5)

Thus from the above equations, it may be determined that the fracture volume capacity, $V_c$, can be related to the selected fracture sealing width, borehole size, rock properties, net pressure and fracture height.

Depending at least in part on the physical characteristics of the formation in which the fracture is formed, a portion of the fluid, $V_{off}$, invaded into the fracture can leak off through pores or fractures of the formation, whereby the fracture volume capacity, $V_c$, can be greater than what is defined above. For example, if $V_{off}$ will have leaked off when the fracture sealing width is reached, the fracture volume capacity, $V_c$, can be the fracture volume capacity as defined above plus $V_{off}$. Thus, the fracture volume capacity will have increased by the amount of the leak-off. If a fracture has permeability much greater than that of its formation matrix and the seal forming time is generally short, $V_{off}$ generally is very small and typically can be omitted. On the other hand, if a volume of fluid, $V_{in}$, has entered a fracture to be sealed before the sealing fluid starts to enter the fracture, $V_{in}$ can cause the fracture pre-inflated and reduce the amount of the sealing fluid that can be contained when the fracture width reaches the fracture sealing width. Therefore, in this case, the fracture volume capacity, $V_c$, can be the fracture volume capacity as defined above deducted by $V_{in}$.

In an embodiment, the fracture volume capacity is calculated from Equations 1 or 2, and 3, 4 and 5. In an embodiment, it is defined by computer simulation of wellbore hydraulic fracturing. In an embodiment, it is defined by a numerical method. In an embodiment, it is defined by a boundary element analysis method. In an embodiment, it is defined by a finite element analysis method. In an embodiment, it is defined by a finite difference analysis method. In an embodiment, it is defined by discrete element analysis method. In an embodiment, it is defined by wellbore hydraulic fracturing experiment.

In an exemplary embodiment, the fracture sealing width is based on the fracture width proximate the fracture mouth and the fracture is sealed proximate to the fracture mouth. In an alternate embodiment, the fracture is sealed at a location inside the fracture other than the mouth. Accordingly, the fracture volume capacity will only include the volume in the fracture tip side behind the sealing location. The volume in front of the seal is connected to the wellbore and, therefore, will not be included when determining the fracture volume capacity.

Fracture sealing with particulates is different from fracture propping. To prop a fracture open to a required width for required stress increase, the particulates with a required size must get into a fracture mouth. Fracture propping requires that the needed right size particulates precisely match the fracture width. However, fracture sealing can happen outside a fracture mouth inside a wellbore. It is okay if some particulates are even much larger than the fracture width at the fracture mouth. Fracture sealing with a particulate sealing fluid requires that the particulates be capable of forming a seal and some of the particulates are still equivalent or larger than the fracture width when forming the seal.

When there are multiple fractures with different fracture volume capacities in the same wellbore interval, if a fracture with the least fracture volume capacity can be sealed, all other fractures can also be sealed because they all have narrower fracture widths with the same volume of invasion fluid. In an embodiment of the present invention, the least fracture volume capacity is calculated when there are multiple weak formations in one wellbore interval or zone within the axial length of the wellbore.

A fracture may intercept a wellbore in any configurations. Different fractures may have different shapes and sizes. Any of these will affect the fracture volume capacity. It is normally impossible to know what fracture configuration is before or during drilling. Because of data uncertainty, a fracture volume capacity defined may not be accurate. It is reasonable to design based on the worst case scenario that has the least fracture volume capacity. When the worst case is satisfied, all other fracture configurations will be satisfied. In an embodiment, the least fracture volume capacity is calculated such that the spurt loss volume is less than or equal to the smallest fracture volume capacity to ensure the sealing of the all possible fractures. For example, the Young's modulus of the formation can be defined with a range of possible values. In an embodiment, the lowest Young's modulus is selected for the minimum fracture volume capacity. In another embodiment, the least fracture volume capacity is defined based on the highest wellbore pressure possible for the selected fracture sealing width. Furthermore, to ensure success, in an embodiment, a fracture volume capacity is calculated to include a safety factor to generate a smaller fracture volume capacity. For example, a fracture volume capacity $V_c$ is redefined by dividing $V_c$ by 1.1.

As stated above, in an exemplary embodiment, the spurt loss volume, $V_{sp}$, of a particulate fracture sealing fluid cannot exceed the fracture volume capacity, $V_c$, for the particulate fracture sealing fluid to seal a fracture. In at least one embodiment, the spurt loss volume of a particulate fracture sealing fluid is defined by laboratory tests. An example of a conventional laboratory test includes evaluating drilling mud pore plugging capability with a filter press based on API (American Petroleum Institute) Recommended Practice 13B-1 (Third Edition, December 2003) and 13B-2 (Fourth Edition, March 2005). This test includes an apparatus generally having a fluid cell on which pressure can be applied to drive a test fluid against a filter paper as a test medium.

According to API Recommend Practice 13I (Seventh Edition, February 2004), another conventional test to determine the capability of sealing larger pores is done by utilizing the Permeability Plugging Apparatus (PPA) against porous ceramic disks with larger pores as a test medium. Additionally, there are low pressure/low temperature (LP/LT) tests and high temperature/high pressure (HT/HP) tests. In the aforementioned tests, typically there is a spurt loss volume, $V_{sp}$, at the beginning of the test when pressure is initially applied to the test cell. The spurt loss volume is the amount of fluid that passes through the filtration medium before a mud filter cake or a tight sealing layer is formed. Typically, the spurt loss fluid contains fine particulates from the mud and, therefore, often is turbid.

Figure 3:
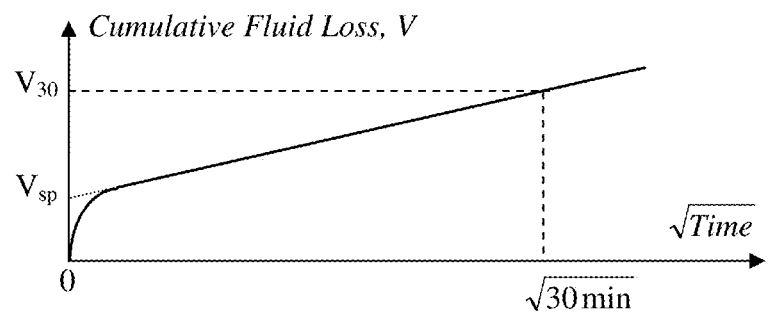
FIG. 3 illustrates a plot depicting the typical cumulative fluid loss over a period of time consistent with an embodiment of the present invention.

In the aforementioned tests, after the spurt loss and formation of a mud filter cake, a steady filtration fluid loss process starts. In the steady filtration fluid loss period, because of the mud cake, only mud filtrate can flow through as the fluid loss. In this period, the fluid collected is a normally particle-free and clear liquid. The fluid loss generally reported is the cumulative fluid loss at 30 minutes or $V_{30}$. The fluid loss, $V_{30}$, therefore includes the spurt loss volume, $V_{sp}$. A plot comparing the cumulative fluid loss during the test against the square root of time will typically resemble the plot illustrated in FIG. 3. As shown in FIG. 3, during the spurt loss period, the plot is a curved line and during the steady filtration fluid loss period, the plot is a straight line. API Recommended Practices 13I and 13B state that the spurt loss volume can be determined by the intercept on the cumulative fluid loss at time=0 by extrapolating the straight filtration line back to time=0. The end of the spurt loss period may be visually judged by observing the fluid loss fluid flowing out of a test cell when the fluid starts to be transparent or solid free. The spurt loss period normally last only for a couple of minutes starting from the beginning of a test. Therefore in one embodiment, the end of the spurt loss period is determined by the time when fluid loss fluid turns transparent. In one embodiment, the spurt loss volume is approximated by the accumulated fluid loss volume at a time less than three minutes.

In an embodiment of the present invention, a method is provided for determining the spurt loss volume of a particulate fracture sealing fluid, wherein the spurt loss volume of a particulate fracture sealing fluid is measured with an apparatus having a fluid cell on which pressure can be applied to drive a test fluid against a filtration media defining a filtration media opening as a test media. Optionally, the filtration medium is a flow restriction medium defining a flow restriction medium opening. In an embodiment, the filtration medium opening is a slot having a slot length and a slot width, wherein the slot width is less than the slot length. In an embodiment, the filtration medium is a slot disk defining a slot having a slot length and a slot width, wherein the slot width is less than the slot length. Optionally, the filtration medium forms a square, oval, or hemi-spherical shape medium defining a filtration medium opening. Optionally, the filtration medium is a flow restriction medium formed from a plurality of flow restriction medium components, wherein the flow restriction medium formed from the plurality of flow restriction medium components defines a flow restriction medium opening. In an embodiment, the flow restriction medium opening is a gap formed by the spacing between at least two of the plurality of flow restriction medium components, wherein the gap is sized and configured to simulate a flow restriction created by a fracture sealing location such as a fracture mouth where a seal is to be formed. It will be appreciated that after reading this disclosure that the fluid cell may be any fluid cell capable of functioning for the intended use and under the applicable pressures to simulate the needed pressure differentials. In an embodiment, the fluid cell is an API fluid loss test cell. Optionally, the fluid cell is a PPA.

Figure 4:
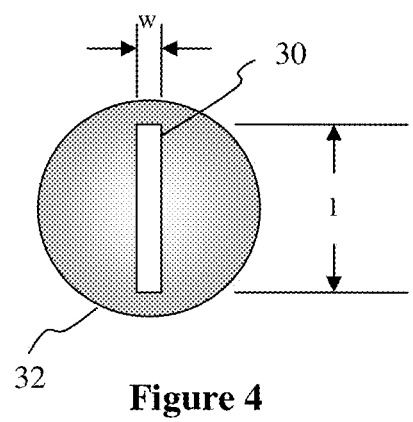
FIG. 4 illustrates a plan view of a slot disk including a slot having a slot width and a slot length, wherein the slot disk is capable of defining the spurt loss volume consistent with an embodiment of the present invention.

In an exemplary embodiment of the present invention, a method is provided for determining the spurt loss volume of a particulate fracture sealing fluid, wherein the spurt loss volume of a particulate fracture sealing fluid is measured with PPA based on API Recommended Practice 13I by changing its filtration medium from a ceramic disk to a slot disk. The slot disk 32 is used to determine the spurt loss volume, $V_{sp}$, over a slot 30 as illustrated in FIG. 4. In an embodiment, the slot disk defines one or more slots. As shown in FIG. 4, the slot disk is a disk defining a slot having a slot length l and a slot width w.

In an exemplary embodiment, the slot disk is approximately 0.25 inch thick. Optionally, the slot disk is greater than 0.25 inch thick. Optionally, the slot disk is less than 0.25 inch thick. Optionally, the slot disk is also tapered and/or varied along its thickness. The slot disk can form a tapering end portion. In an embodiment, the slot width is constant throughout the thickness of the slot. The slot can form any shape as long as it has a slot length and a substantially constant slot width, wherein the slot width is less than the slot length. For example, the slot may be rectangular. In an exemplary embodiment, the slot 30 defined by the slot disk 32 is rectangular in shape and has a length l and width w as shown in FIG. 4.

Figure 9:
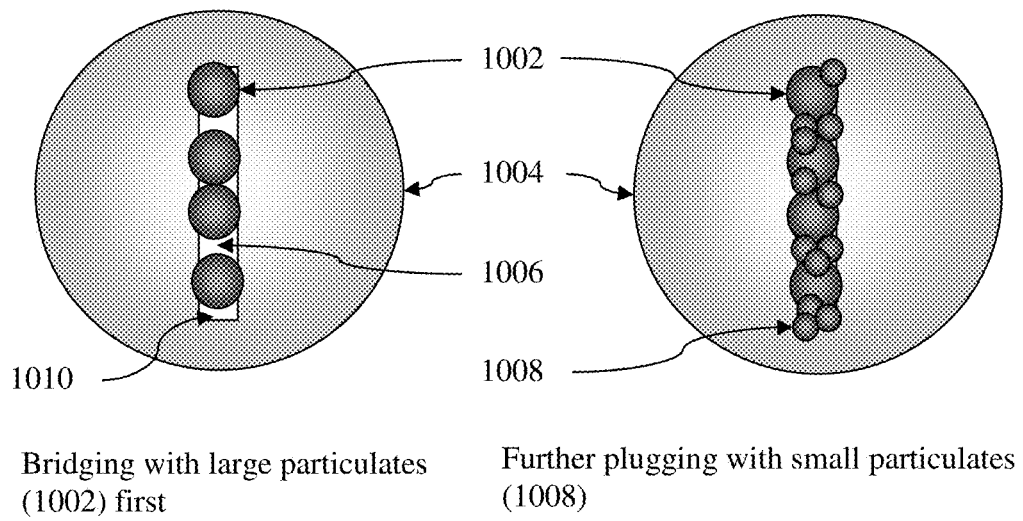
FIG. 9 illustrates bridging particles bridging off the slot leaving gaps between them for smaller particles to plug.

In an exemplary embodiment, the filtration medium includes a slot disk. The sealing behavior of a particulate fracture sealing fluid with a slot disk possesses similarities to that of a drilling fluid with a filter paper as the filtration medium. In particular, during a test for a particulate fracture sealing fluid with a slot disk, after applying pressure to the fluid in a PPA test cell, before an effective seal has formed, a portion of the fluid will flow out of the slot and is collected and measured in volume during the test period. This is the spurt loss volume, $V_{sp}$, of the fluid over the selected slot. In FIG. 9, carried by fluid, large bridging particulates 1002 may bridge off at the slot 1010 leaving gaps 1006 between them for small particulates 1008 to plug. Smaller gaps between these small particulates then can be plugged off by fine particulates. Eventually with colloidal particles such as clay and fluid loss agents in a fluid, the permeability of the seal can be soon reduced to very small and only the carrying liquid such as water or oil can slowly pass through. As shown in FIG. 9 for an embodiment, regarding the slot disk 1004, there must be enough accumulation of large particulates 1002 approximately equal or larger than the slot width on the slot 1010 to bridge off the slot first so that the small particulates 1008 can plug the gaps 1006 between those bridging particulates 1002. Then the fine particulates contained in a base fluid such as in a drilling mud begin to form a mud cake to start the filtration control process. If there are no particulates large enough to bridge off the slot, an effective seal cannot form before the entire test fluid in the test cell flows through the slot. If there are only large bridging particulates, only a loose pack of the particulates can exist at the slot and a tight seal can not form. All of the test fluid will soon flow out of the test cell through this loose pack under the test pressure differential. When the particulate fracture sealing fluid is appropriate, an effective seal can form rapidly and the spurt loss volume can be very small. In an embodiment the particulate fracture sealing fluid includes a quantity of small particles capable of sealing the gaps between the large bridging particles. In an embodiment the particulate fracture sealing fluid includes a quantity of large particulates capable of bridging off the slot.

The spurt loss volume over a slot disk can be defined by the same method stated in API Recommended Practice 13I as for fluids tested on a ceramic disk. The spurt loss tested on a slot disk is a close measurement of the spurt loss volume of a particulate fracture sealing fluid over a fracture of a width the same as the slot width. The cumulative fluid loss during the test plotted against the square root of time will follow the plot as illustrated in FIG. 3.

Generally, the spurt loss fluid of the particulate fracture sealing fluid, designed to seal a fracture mouth at a fracture sealing width, w, and driven by high wellbore pressure, enters a leaking fracture and opens the fracture wider and grows it longer. In order to arrest the fracture growth, the spurt loss period must have completed so that an effective seal can form by the time the fracture mouth grows to reach the fracture sealing width. In other words, the spurt loss volume must not be greater than the fracture volume capacity, $V_c$, or what the fracture can contain when its fracture mouth grows to reach the fracture sealing width. If the spurt loss volume is greater than $V_c$, an effective seal cannot form when the fracture is as wide as the fracture sealing width. Further invasion of fluid will open the fracture wider and beyond what the fracture sealing fluid can seal any more. Without forming this seal, the fracture will continue to grow causing lost circulation or lost returns. Therefore, for the fracture sealing width, w, to make an effective fracture sealing fluid, the spurt loss volume of the sealing fluid cannot be larger than the fracture volume capacity, $V_c$. Thus, in an exemplary embodiment, the spurt loss volume of the sealing fluid is less than or equal to the fracture volume capacity, $V_c$.

In an embodiment of the present invention, a comparison between spurt loss volume and fracture volume capacity can be made by converting the spurt loss volume measured with a slot having a slot length, 1, to an equivalent spurt loss volume for the fracture height. For example, if the spurt loss volume of a sealing fluid measured on a slot disk having a slot length, 1, of 5 inches is 0.25 inch$^3$ and the fracture height, H, of the fracture to be sealed is 200 inches, in order to form a fracture seal, the fracture volume capacity of the fracture must be equal to or greater than this total spurt loss volume equivalent for the total fracture height and is 0.25/5.200=10 inch$^3$.

In an embodiment, the slot length, 1, varies for a slot disk having a constant slot width, w, for testing. For example, a slot disk has a slot length of 50 mm and a slot width of 300 microns. Optionally, the slot disk has a slot length of 75 mm and a slot width of 300 microns. Thus, it is desirable to quantify the spurt loss volume in a uniform manner to link the spurt loss volume to fracture sealing. Accordingly, in an embodiment of the present invention, the spurt loss volume, $V_{sp}$, can be converted into a unit slot length spurt loss volume, $V_{usp}$, by dividing $V_{sp}$ by the slot length, 1, as follows:

$$V_{usp}=V_{sp}/l \quad \text{(Equation 6)}$$

Similarly, the fracture height, H, of a fracture can vary. Thus, it is desirable to quantify the fracture volume capacity, $V_c$, in a uniform manner to link the fracture volume capacity to fracture sealing. Accordingly, in an embodiment of the present invention, the fracture volume capacity can be converted into a unit height fracture volume capacity, $V_{uc}$, by dividing $V_c$ by the fracture height, H, as follows:

$$V_{uc}=V_c/H \quad \text{(Equation 7)}$$

If a fracture can be viewed as illustrated in FIG. 2, based on Equation 5, it is not necessary to know the fracture height for the unit height fracture volume capacity. The unit height fracture volume capacity is equal to A, the pressurized fracture cross section area from the wellbore wall to the fracture tip. This is because, based on Equation 5, $$V_{uc}=V_c/H=(A \cdot H)/H=A \quad \text{(Equation 8)}$$

In an exemplary embodiment of the present invention, a characteristic of an effective particulate fracture sealing fluid to seal a fracture having a selected fracture sealing width w, includes a unit slot length spurt loss volume, $V_{usp}$, being less than or equal to the unit height fracture volume capacity, $V_{uc}$, for the fracture. When the fracture is quickly sealed, the wellbore is immediately strengthened and the higher wellbore pressure can be contained. A fluid with a smaller $V_{usp}$ or tighter control on the spurt loss volume on the same slot width can arrest fracture growth earlier and therefore has a higher fracture sealing capability.

In an exemplary embodiment, the selected fracture sealing width of the slot is selected to be substantially equivalent to the width of the fracture mouth. However, the selected target width of the slot can also be wider than the width of the fracture to be sealed. A particulate fracture sealing fluid tested with a wider slot for the same unit slot length spurt loss volume simply has a greater sealing capacity.

Quantifying the spurt loss volume in terms of the unit slot length spurt loss volume allows for different particulate fracture sealing fluids to be compared as long as the slot width is equivalent. For example, if Formulation A has a unit slot spurt loss volume of 2 ml/inch against a slot of 500 microns wide and Formulation B has a unit slot spurt loss volume of only 1 ml/inch against a slot of the same width, Formulation B has a tighter control on sealing a fracture than Formulation A. There can be an unlimited number of particulate fracture sealing fluids. However, when characterized with the unit slot length spurt loss volume, the particulate fracture sealing fluids can be easily compared.

During a drilling process with particulate sealing fluid, the particle size degradation may occur and this may change the spurt loss control of a formulation. It is therefore meaningful to have quality control on the spurt loss at a rigsite. In an embodiment, quality control on the spurt loss is implemented. In another embodiment, quality control on the spurt loss by testing the sealing fluid against a slot disk with slots of a slot width equivalent to the selected fracture sealing width.

Figure 5:
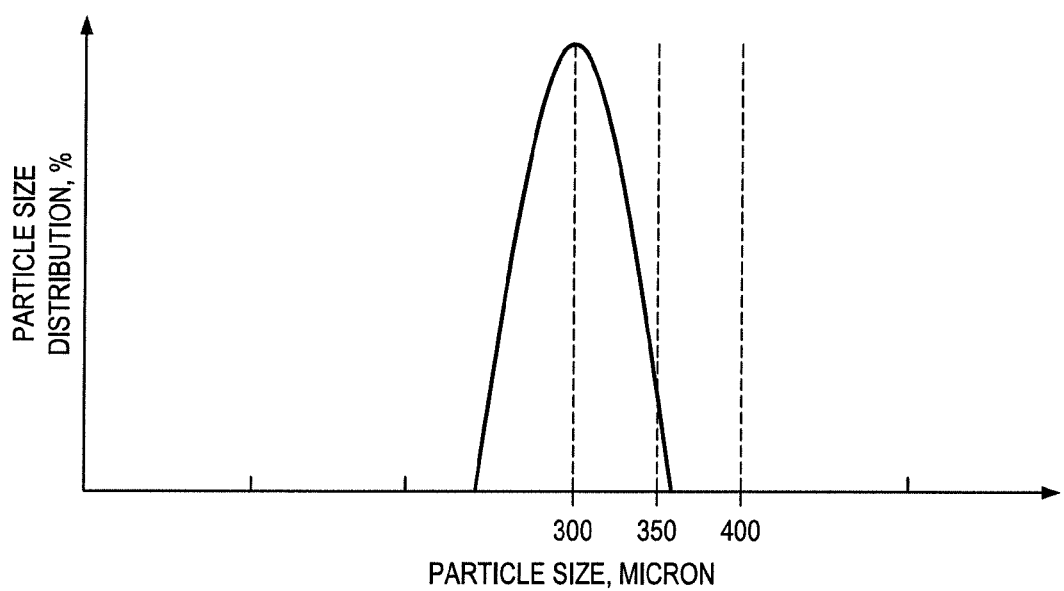
FIG. 5 illustrates a plot depicting a particle size distribution of bridging particles in a fracture sealing composition in relation to three fracture widths at a fracture location at which the fracture is intended to be sealed.

Generally, the fracture sealing composition can be optimized specifically based on the fracture width to be sealed. The particulates for fracture sealing are typically not equivalent in size. An optimized fracture sealing composition typically includes a component of large bridging particles that are equivalent to the fracture width at the fracture location wherein the fracture will be sealed. For optimized sealing purposes for a specific fracture width, the particulate size distribution of this component is preferred narrow and comparable to a normal distribution. In the optimized fracture sealing composition, other components of small particles are generally desired for plugging the gaps between those large bridging particles and eventually only filtrate can pass through the formed seal. For example, for sealing a fracture of a 300 micron fracture width, to be optimized for forming the seal, the particle size distribution of the component of large particulates of the fracture sealing composition would be centered around 300 micron as indicated in FIG. 5. Accordingly, most of the large bridging particles will be equivalent to the fracture width. Therefore, an optimized fracture sealing composition for a fracture width is typically not optimized for sealing a larger fracture width. For example, an optimized fracture sealing composition for sealing a fracture of 300 micron wide is less efficient to seal a 350 micron wide fracture. Specifically, for a 400 micron wide fracture, the sealing composition may be generally no longer useful for sealing the fracture since the fracture width is much greater than the width the particulates can seal.

A slot can be used to represent the entrance of a long fracture at the wellbore. A pore throat is the narrowest passageway of a round pore in a permeable rock. It will be appreciated that after reading this disclosure that bridging off a slot differs from bridging off a pore throat. For example, particle bridging off a pore throat may occur when the particles are only ⅓ to ⅔ of the pore throat size. However, to bridge off a slot, the particulates have to be substantially equivalent to or larger than the slot width. A fluid capable of bridging off a pore throat of 100 microns in diameter may not be able to bridge off a slot of 100 micron in width. However, a fluid capable of bridging off a 100 micron slot can bridge off a pore throat of 100 microns in diameter. In at least one embodiment of the present invention, the particle size of at least one particle in the particulate fracture sealing fluid is substantially equal or larger than the fracture to bridge off a fracture of width, w. Optionally, in one embodiment, the volume of the particulates that have at least one dimension 100 to 150 percent of a selected fracture sealing width is 5 to 35 percent of the total volume of all the sealing particulates in a sealing composition.

Because the physical size and shape of a fracture differ from a pore throat, a particulate fracture sealing fluid cannot be evaluated against a filter paper or porous ceramic disk as defined in API Recommended Practice 13B and 13I. Due to the different sizes and shapes of the fluid passageways inherent in filter paper, ceramic disks and slot disks, the spurt loss volumes obtained from different test media have no correlation, even compared at the same passage area. For example, a fluid that has a spurt loss of 1 ml against a filter paper may have a spurt loss of 5 ml against a disk with a slot of 500 micron wide and 1 inch long. Another fluid that also has a spurt loss volume of 1 ml against a filter paper may have a spurt loss volume of 10 ml against a disk with a slot of 500 micron wide and 1 inch long. Conventionally, drilling fluid has been designed to minimize the spurt loss volume against a filter paper. Drilling fluid may have a close to zero spurt loss volume against a filter paper. Conventional drilling fluid normally has only colloidal particles. Even with weighting materials such as barite of maximum particle size less than approximately 100 micron, it cannot bridge off a 500 micron wide slot and will lose all its test fluid in a test cell without sealing off the slot. In other words, a conventional drilling fluid that has a close to zero spurt loss volume and a close to zero 30 min fluid loss on a filter paper may have an infinite high spurt loss against a slot click with a 500 micron wide slot.

Figure 6:
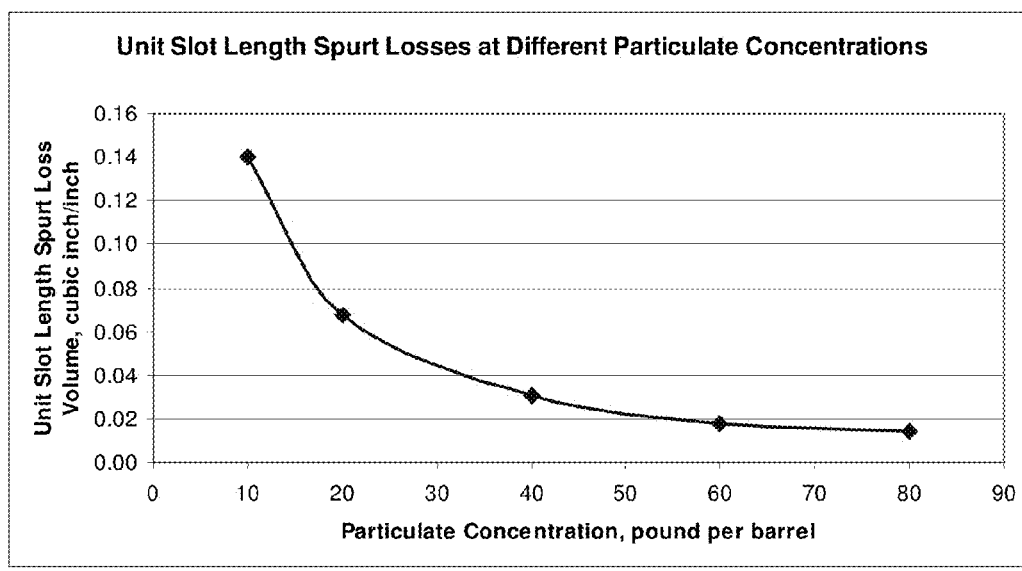
FIG. 6 illustrates a plot depicting the spurt loss volume at different concentrations of a particulate composition over the same slot consistent with an embodiment of the present invention.

In an embodiment wherein particulate fracture sealing fluid having different particulate concentrations are fed through respective disks having equivalent slots, the disk through which the higher concentration of the particulates is fed experiences faster sealing or a smaller spurt loss volume, and the disk through which the lower concentration of particles is fed forms the seal later or provides a larger spurt loss volume. Thus, in an embodiment, a particulate composition for fracture sealing can be characterized by the relationship between the unit slot length spurt loss volumes of the particulate composition at one or more concentrations in a drilling fluid defined by testing with a PPA using a slot disk as the filtration medium. FIG. 6 illustrates a plot indicative of spurt loss volumes at different concentrations of a version of a commercial particulate sealing composition STRESS-SHIELD™ (a product offered by Sharp-Rock Technologies, Inc.). As shown in FIG. 6, a particulate fracture sealing fluid has a higher sealing capability when it has a smaller unit slot length spurt loss volume on the same slot width or the same unit slot length spurt loss volume on a wider slot compared at the same concentration. Therefore, a particulate fracture sealing fluid has a higher sealing capacity if its unit slot length spurt loss volume is smaller on a larger slot width at the same concentration.

In an exemplary embodiment, a particulate fracture sealing fluid includes a base fluid and a particulate composition including fracture sealing particles. The overall particle size distribution of the fluid may range from 1 nanometer to 5000 microns. In an embodiment, the base fluid is drill-in fluid. In another embodiment, the base fluid is cement slurry. In another embodiment, the base fluid is completion fluid. In another embodiment, the base fluid is spacer fluid. In another embodiment, the base fluid is workover fluid. In another embodiment, the base fluid is a drilling fluid and, optionally, the drilling fluid is a drilling mud. The drilling mud for the particulate fracture sealing fluid can be any kind, including but not limited to water based mud, oil based mud, synthetic based mud, completion fluid, spacer fluid, cementing fluid, drill-in fluid, or wash fluid. It can also be water, oil or brine. Oil based mud and synthetic based mud are typically superior in controlling fluid loss to water based mud. Thus, in an exemplary embodiment, the fracture sealing particles are added into an oil based mud or synthetic based mud to have a lower mud cake permeability or tighter control on filtrate leaking through the formed seal at or near the fracture mouth for a long term sealing stability. A regular drilling mud normally contains clay in water based fluid or organoclay in oil based or synthetic based fluid. The drilling fluid can also contain fluid loss control additives, together with the clay particles, to form a mud cake to control drilling mud filtration loss into permeable formations. Weighting materials can also exist in the drilling fluid. A drilling fluid normally has a low HT/HP (High Temperature/High Pressure) fluid loss and a low spurt loss volume with a filter paper as the filtration medium.

In an exemplary embodiment, particles for the particulate compositions include but are not limited to one or more of the following materials: calcium carbonate, sand, coke, petroleum coke, graphite, resilient graphitic carbon, synthetic graphite, cedar fiber, nut hulls, corn cobs, fiber, synthetic fiber, paper, threaded paper, ground paper, carbon fiber, threaded rug, asphalt, gilsonite, rubber, foam rubber, drilled cuttings, saw dust, mica, wood chips, engineering plastics, hollow spheres, hollow plastic spheres, hollow glass spheres, fly ash, cotton seed hulls, walnut hulls, pistachio hulls, almond hulls, peanut hulls, cement, clay, bentonite, modified clay, organoclay, limestone, dolomite, marble, resin particles, metal particles, ceramic particles, weighting materials such as barite, hematite, iron oxide, ilmenite, and combinations thereof. Optionally, nanotechnology particles, e.g., silica nanoparticles, clay nanoparticles, and the like are used for the compositions. Optionally, chemically treated particles are used for the compositions. The chemically treated particles can include resin coated, surface sticky, surface hydrophobic and surface hydrophilic particles. In an exemplary embodiment, the fracture sealing composition remains consistent throughout the method of sealing the wellbore. In such an embodiment, the type of particulate, e.g., peanut hulls and/or limestone, will remain the same throughout the method of sealing the wellbore. The wellbore strengthening effect is determined at least in part by the strength of the seal, and the seal strength is determined at least in part by the strength of the particles. Correspondingly, sealing particles having a high material strength are desirable for providing a high wellbore strength. Thus, in an exemplary embodiment of the present invention, resin particles, metal particles, ceramic particles, carbon fiber particles, or nanotechnology particles are used in a wellbore requiring high wellbore strength.

The shape of the particles can be granular, flake and/or fibrous. Particle surface properties such as hydrophobic and hydrophilic properties can affect the packing efficiency of the particles. Particle resiliency may also affect the packing efficiency of the particles.

The size of the particles in the particulate fracture sealing fluid can vary in at least one embodiment. Accordingly, to seal a slot of fracture sealing width, w, it is desirable for a portion of the particulate fracture sealing fluid to include large particles having at least one dimension (e.g., length, height, width, or diameter) greater than or approximately equal to the fracture sealing width. Additionally, it is desirable for a portion of the particulate fracture sealing fluid to include small particles having a dimension less than the large particles, wherein the small particles are capable of sealing the gaps between the large particles. Furthermore, it is desirable for a portion of the particulate fracture sealing fluid to include even smaller particles capable of sealing the gaps between those small particles to form a tight seal packing until the colloidal particles and fluid loss agents in the drilling fluid can seal the packing off and only filtrate can flow through it. Without the smaller particles to seal off the gaps between those larger particles, the accumulation of the particles can only be loosely packed and the fluid including smaller particles can still pass through the accumulation of the larger particles. All fluid passing through the accumulation of those particles of different sizes before a tight seal is formed is the spurt loss. This spurt loss volume is not a direct function of any portion of the particulate composition and it is a collective result of sealing from all particulates. Without a good particle size distribution, even when there are large and small particulates present in a fluid, a large concentration of the particulates with a large portion of its size larger than the slot width may not be able to form a seal. With a good particle size distribution, the particulate composition with only a small portion of particulates larger than the slot width can form a seal and generate a very small spurt loss volume. Therefore a spurt loss volume can not be calculated only based on a portion of a particulate composition. The particle size distribution can be optimized by lab tests by modifying the composition to minimize the spurt loss volume. This demonstrates the need for quality control during manufacture of the composition and during operation of the composition at the rig site.

Spurt losses have been measured for various compositions to optimize the sealing efficiency or to minimize the spurt loss. The following are lab test results for six particulate compositions with four different particulate components. The lab tests were done in a fluid loss test cell against a slot disk. The slot disk has slots of 350 micron wide. The base fluid for the tests is a water solution of 0.3% XC biopolymer so it is a solid free fluid. The total concentration of the particulates is 20 pound per barrel. The four components are 40 mesh walnut hulls, 200 mesh walnut hulls, 600 mesh Calcium Carbonate and 2000 mesh Calcium Carbonate and their nominal sizes are 375 micron, 75 micron, 25 micron and 7.5 micron respectively. So the 40 mesh walnut hulls have the largest particulate size. The spurt loss of each test is measured according to the API Recommended Practice 13I. The components of the compositions and corresponding spurt losses are listed in Table 1 below utilizing standard API mesh sizes:

TABLE 1

Spurt Losses for Different Particulate Sealing Compositions

| Composition | Component | Volume % | Spurt Loss, ml/ft |
|---|---|---|---|
| step-down 2-4 | 40 mesh walnut hulls | 25 | 9.8 |
| | 200 mesh walnut hulls | 35 | |
| | 600 mesh Calcium Carbonate | 25 | |
| | 2000 mesh Calcium Carbonate | 15 | |
| step-down 2-4(4) | 40 mesh walnut hulls | 25 | 11.8 |
| | 200 mesh walnut hulls | 35 | |
| | 600 mesh Calcium Carbonate | 20 | |
| | 2000 mesh Calcium Carbonate | 20 | |
| iso-v | 40 mesh walnut hulls | 25 | 17.0 |
| | 200 mesh walnut hulls | 25 | |
| | 600 mesh Calcium Carbonate | 25 | |
| | 2000 mesh Calcium Carbonate | 25 | |
| Step-down 2-4(6) | 40 mesh walnut hulls | 45 | 21.2 |
| | 200 mesh walnut hulls | 30 | |
| | 600 mesh Calcium Carbonate | 15 | |
| | 2000 mesh Calcium Carbonate | 10 | |
| Step-down 2-4(8) | 40 mesh walnut hulls | 30 | 14.5 |
| | 200 mesh walnut hulls | 45 | |
| | 600 mesh Calcium Carbonate | 15 | |
| | 2000 mesh Calcium Carbonate | 10 | |

For Composition step-down 2-4, step-down 2-4(2) and iso-v, the spurt loss is 9.8, 11.8 and 17.0 respectively. The component of 40 mesh walnut hulls remains the same as 25% for all the three compositions. Difference in spurt losses for these three compositions clearly indicates that spurt losses are also affected by the components of smaller particulate sizes. For Composition step-down 2-4(8) and step-down 2-4(6), the component of 40 mesh walnut hulls or the component with the largest particulate size has increased from 30% to 45%. However, the corresponding spurt loss does not decrease with the increase. Composition step-down 2-4(6) that has the larger percentage of the largest component even has a larger spurt loss than the Composition step-down 2-4(8), which contains less percentage of the largest component or 40 mesh walnut hulls.

It has been found during lab tests that many compositions even when they have particulates larger than the slot width do not form a seal indicated by losing all test fluid in a test cell within approximately one or two minutes. Even for those compositions that eventually form a seal, the spurt loss volume is not a function of the component of the largest size or any individual component in the sealing composition. It is a collective result of all particulates in the composition.

However, for a specific particulate sealing formulation with a fixed composition, when a seal can form, higher concentrations do show smaller spurt losses. Even in this case, the relationship between the concentration and the spurt loss volume is not linear as shown in FIG. 6. Furthermore, different formulations may have different the relationships between concentrations and spurt loss volumes.

It is impossible to know for sure the spurt loss volume without a lab test that simulates the fracture sealing process. There is no direct relationship that can be used to calculate a spurt loss volume based on the concentration of the component of the large bridging particulates or any particulates in a composition.

Lab tests indicate that the spurt loss volume is not linearly related to the concentration of a particulate composition (FIG. 6) and it is specific to its testing filtration medium. Lab tests show that, in order to minimize spurt losses, the volume of the particulates that have at least one dimension 100 to 150 percent of a selected fracture sealing width is preferred to be from 5 to 35 percent of the total volume of all the sealing particulates in a sealing composition. Other smaller particulates can be further optimized by spurt loss tests. Optionally, the sealing fluid includes a broad range of particles size distribution, wherein the sealing fluid includes a smooth/continuous range of particle sizes ranging from 1 nanometer to 5000 microns. In an alternate embodiment, the particle size distribution is designed to include formation of a particulate seal inside the fracture after the fracture mouth has been sealed and the fracture closes after its trapped pressure bled off.

In an exemplary embodiment, the concentration of a particulate composition in a sealing fluid is defined by the required unit slot length spurt loss volume for the corresponding particulate fracture sealing fluid. In an embodiment, the required concentration of a particulate composition is at least 0.1 pound per barrel. Optionally, the required concentration of a particulate composition for the corresponding fracture sealing fluid is between 0.1 and 300 pounds per barrel. In an exemplary embodiment, the required concentration of a particulate composition for the corresponding fracture sealing fluid is between 5 and 100 pounds per barrel. In an exemplary embodiment, the particulate concentration of the sealing fluid is manipulated to adapt to changing drilling parameters to seal the fracture formed in the wall or the wellbore of the hydrocarbon well.

It will be understood by one of ordinary skill in the art that there can be an unlimited number of fluid formulations that can achieve the same spurt loss volume against a slot. Factors or variables including particle size distribution, surface roughness, particle interaction, individual particle shapes, individual particle strength, particle density, various combinations, resiliency, modulus, brittleness and surface charges can all be varied in differing amounts. Furthermore, without a suitable quality control, the same particulate material manufactured out of the same process can vary substantially from batch to batch. In an exemplary embodiment, a lab test for the spurt loss is conducted to ensure the formulation achieves the required control.

One or more fractures can be penetrated by a wellbore. In an exemplary embodiment, the particulate fracture sealing fluid is designed for the fracture having the smallest fracture volume capacity to ensure it is capable of sealing all fractures. Particularly in wellbores including multiple fractures, designing the particulate fracture sealing fluid to seal the fracture having the smallest fracture volume capacity is desired as such a design can seal those having larger fracture volume capacities. In such an instance, as the fracture having the smallest fracture volume capacity reaches the fracture sealing width, other fractures should all have a narrower width. In such a design, the particulate fracture sealing fluid is capable of sealing all the fractures that may exist in the wellbore.

It will be understood by one of ordinary skill in the art that the particulates can seal without entering into the fracture. In an embodiment, the placement of particulates across the fracture width of a sealed fracture is sustained by fluid pressure. The particulates can differ in size in relation to the fracture mouth and can be capable of sealing off the fracture. In one embodiment, one or more particulates can be substantially larger than the fracture mouth. In an embodiment wherein a higher than necessary concentration of a particulate composition is applied, the fracture width will not grow to the selected width at the time when an effective seal has formed at the fracture mouth.

Generally, a fracture width is basically zero when the fracture is substantially closed. Typically, a leaking fracture may not be substantially closed and may have an initial width. Such a width can be expanded when more fluid enters the fracture and pressurizes the fracture surface. Thus, to seal a leaking fracture, a fracture sealing width larger than this initial width can be selected to achieve an effective sealing. In an embodiment, the leaking fracture has an initial width, wherein the initial width is greater than zero. To ensure that a particulate fracture sealing fluid is suitable for all fractures, it is desirable to take into account the initial fracture width in selecting the fracture sealing width. The fracture sealing width in an embodiment is greater than the initial fracture width. The fracture sealing width to be sealed can be selected based on different criteria. Such criteria can include how easy the fracture is to seal and/or may be based on a desire for a low solid content in the mud, solid control efficiency, economy, a required high seal strength or logistics. In an embodiment, the fracture sealing width ranges from 5 microns to 5000 microns. Optionally, the fracture sealing width ranges from 200 to 1500 microns. In an exemplary embodiment, the fracture sealing width ranges from 300 microns to 1200 microns.

It has been determined that high fracture sealing capability is reached when a particulate fracture sealing fluid has an approaching zero unit slot length spurt loss volume against a very wide slot width. Therefore, in an embodiment of the present invention, a high sealing capacity particulate fracture sealing fluid having an approaching zero unit slot length spurt loss volume against a very wide slot can be used to successfully drill through weak formations without acquiring detailed knowledge regarding the fracture volume capacity for the formation as long as the fracture volume capacity can not be this small in any circumstances.

It will be understood by one of ordinary skill in the art that a sealed fracture will typically stabilize and cease growing. After the fracture propagation is arrested by the formed seal, the fracture will relax and eventually be closed by the near wellbore hoop stress when the trapped fluid gradually leaks off into formations through the fracture surface and into unopened part of the leaking fracture.

Due to fracture stability consideration, in an embodiment of the present invention, it is desirable for the sealing particles to be made of impermeable materials to favor a low filtration rate at the seal. Additionally, in embodiments wherein fracture openings do not have to be propped wide for higher compressive stress, low compressive strength materials can be used, including flexible fibers capable of sealing the fractures. In at least one embodiment, the particulates sustaining the fracture width form a seal inside the fracture. The additional seal formed by the particulates inside the fracture can provide an additional sealing effect. Thus, in an alternate embodiment, the particle size distribution can include a relatively higher concentration of particles smaller than fracture mouth width to assist in also forming a seal inside the fracture when the fracture is closing.

In an embodiment, the particulates include drilled cuttings. Drilled cuttings may be sized and configured to help control the spurt loss volume. For example, suitably-sized cuttings can be generated by designed drill bits and/or altered by use of designed hardware, e.g., shale shaker, or the drill string or casing. Utilizing particulates or drilled cuttings to control spurt loss volume can require the removal of a multitude of inappropriately sized cuttings or other unusable cuttings from the sealing fluid in order to maintain the designed property of the wellbore strengthening formulation. Because drilled cuttings or debris are mixed with the designed formulation during drilling, solid control equipment can be designed to collect and dispose of the unusable cuttings. In an embodiment, solid control equipment such as a shale shaker is used to retain the needed particulates in the fluid while discarding the unwanted drilled cuttings.

In the field, the spurt loss volume of the particulate fracture sealing fluid can increase, for example, due to particulates in the mud being shattered causing size degradation over time or potential drilled cuttings contamination. Continued addition of particulates may be needed to maintain the required spurt loss control, especially for drilling through a long weak interval. Therefore, in an exemplary embodiment of the present invention, the spurt loss volume of the particulate fracture sealing fluid against a slot disk defining a slot having a slot width equivalent to the fracture sealing width is monitored during the application of the sealing fluid to ensure the designed spurt loss volume is maintained at all times.

In some cases, portions of the wellbore are encased in well casing. Only a newly drilled portion of the well bore is exposed and the well bore wall may require strengthening. In an embodiment, the particulate fracture sealing fluid is applied to a weak wellbore by drilling the weak formation while circulating the formulation to the bit. In this way, the weak formation can be sealed and the weak wellbore strengthened immediately when it is exposed by drilling. This is a strengthening while drilling scenario. Optionally, the particulate fracture sealing fluid is applied after a weak wellbore has been created. In an embodiment, the particulate fracture sealing fluid is applied after lost circulation has happened. In an embodiment, the particulate fracture sealing fluid is applied before lost circulation has happened. In an embodiment, the high mud weight or density mud can be converted into a particulate fracture sealing fluid by adding a designed particulate composition at a needed concentration. The low weight mud can be displaced by the high weight fracture sealing mud. Thereafter, the well can be drilled with the high mud weight particulate fracture sealing fluid to avoid fracturing the drilled weak formation. Alternatively, the low weight mud can be converted into a particulate fracture sealing fluid by adding necessary particulates based on engineering design. The mud is then increased in density before drilling with the higher density mud. It is not necessary to circulate the fracture sealing fluid for the entire wellbore. For strengthening an existing weak wellbore, only the weak wellbore interval is needed to be filled with the sealing fluid. In an embodiment, the particulate fracture sealing fluid is pumped to fill the weak wellbore interval and its volume is only enough for sealing the weak wellbore interval. Optionally, pressure is applied to the weak wellbore to ensure the wellbore is strengthened to the needed pressure integrity or strength when the particulate fracture sealing fluid is in the weak wellbore interval.

During running steel casing into a wellbore, higher wellbore pressure may be experienced and break down the wellbore. In an embodiment, a fracture sealing fluid is circulated to a weak wellbore interval before running steel casing into the wellbore to prevent induced fluid losses during running casing. During cementing the steel casing with cement slurry, higher wellbore may be experienced. In one embodiment, a fracture sealing composition is to the spacer fluid used to separate the cement slurry and regular wellbore fluid to strengthening the wellbore during cementing. In another embodiment, a fracture sealing composition is added directly to the cement slurry to strengthen a wellbore during cementing. In another embodiment, a fracture sealing composition is added in a wellbore fluid in a wellbore before pumping cement slurry for cementing the casing to strengthen the wellbore during cementing.

Figure 8:
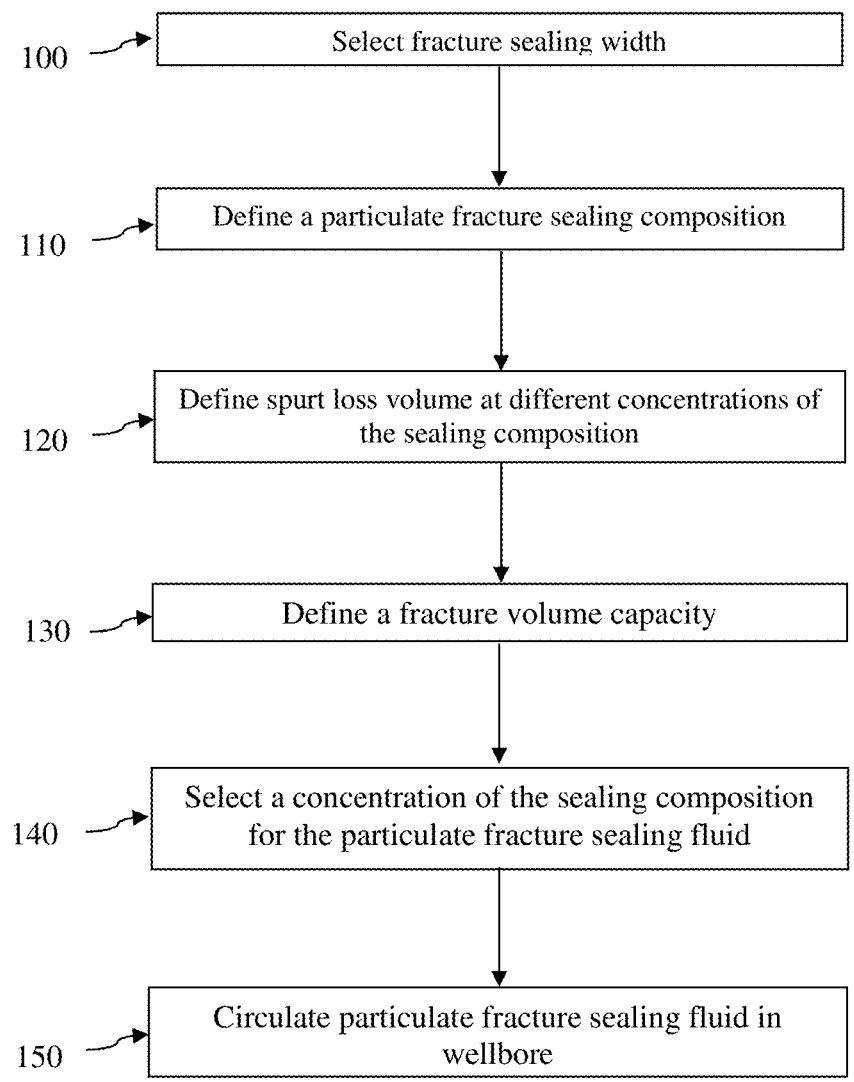
FIG. 8 illustrates a schematic illustrating a simplified flow chart consistent with an embodiment of the present invention.

Turning now to FIG. 8, a simplified flow chart illustrates an overview of a method for sealing a fracture in a weak wellbore provided in one embodiment of the present invention. As illustrated in block 100, a fracture sealing width is selected, wherein in the present embodiment the fracture sealing width is the fracture mouth width to be sealed for strengthening a weak wellbore. In the embodiment of FIG. 8, the selected fracture sealing width is fixed and remains constant throughout the method. In block 110, a fracture sealing composition formed from one or more particulates is selected based on the selected fracture width. In block 120, the selected fracture sealing composition at different concentrations in drilling fluid is tested with a PPA for its unit slot length spurt loss volumes, whereby, in the illustrated embodiment, the particulate fracture sealing fluid in the PPA is flowed under wellbore pressure through a slot disk defining a slot having a slot width equivalent to the fracture sealing width. In block 130, the unit height fracture volume capacity can be obtained using Equations 2, 3, 4, and 8, wherein the wellbore radius, R, and the formation mechanical properties, v, E, and net pressure $\Delta P$ are known. Block 140 illustrates selecting a concentration of the fracture sealing composition to satisfy a criterion: the unit slot length spurt loss volume is less than or equal to the unit height fracture volume capacity. The fracture sealing composition is selected at least in part on the selected fracture sealing width. In the illustrated embodiment, the composition of the one or more particulates is fixed and remains unchanged and equally suitable for sealing the selected fracture sealing width throughout the method. If there is a need to change any well conditions, the change required is in the fracture volume capacity in Block 130 and the selected concentration of the sealing composition in Block 140. Other components of the method are not affected. In other words, any well condition change can be adapted by the change in the concentration of the sealing composition. In an alternate embodiment, the order of Block 120 and Block 130 may be switched.

The capability of optimally adapting to new drilling conditions by the modification of only the concentration of the particulate fracture sealing fluid is advantageous to drilling operations at the rig site. In this way, the composition of the particulates remains optimized without having to be changed, which allows for the particulate to be mass manufactured for a pre-selected fracture width. Additionally, quality-control for the performance of the particulates is beneficial to perform at the factory when manufacturing the particulate composition. Furthermore, a filtration medium defining a filtration medium opening used in testing the sealing fluid as discussed below can be used for each batch and the opening does not have to be modified in size for differing batches. Still further, inventory at the rig site is easier to stock as the particulates to be used will be known and will not need to be changed. Also, uncertainties in drilling parameters may be better managed through the consistent use of the same particulate. Furthermore, the composition of the particulate remains optimized for sealing the fracture. Components of solid control systems, such as a shale shaker screens, do not require modification such as the changing of mesh size when drilling conditions change, because the particle size distribution of the composition will not change when only the concentration of the particulates in the sealing fluid is changed.

Wellbore strengthening fluid is created at the drill site by combining well drilling fluid with particulate sealing composition. It will be understood that well drilling fluid is continually pumped downhole to the drill bit. The well drilling fluid is circulated back to the surface in the annulus formed between the wall of the well bore and the drill string. The well drill fluid is optionally circulated through shale shakers. Drill cuttings are removed from the drilling fluid by the shale shakers. The circulation loop can include additional equipment such as fluid holding tanks and hoppers. Quantities of particulate sealing composition can be poured and mixed into the well drilling fluid using hoppers. The combined particulate sealing component and well drilling fluid can then be pumped into the drill string. Quality control can be performed on the combined fluid to ensure it demonstrates the engineered spurt loss.

When the spurt loss generated by the particulate fracture sealing fluid indicates in the testing in block (120) in the embodiment of FIG. 8 that the spurt loss fluid can be contained by the fracture when the effective seal is formed, it is indicative that the sealing fluid can seal the fracture before it grows too wide. When the fracture is effectively sealed, the wellbore is strengthened. Optionally, because any sealing formulation with smaller spurt loss volumes will also indicate the ability to effectively seal the fracture. In an embodiment, for engineering safety factor consideration, a particulate fracture sealing fluid with a slightly smaller spurt loss volume is selected. Thus, in block (150) of the embodiment of FIG. 8, the wellbore is circulated with the selected particulate fracture sealing fluid containing the selected concentration of the fracture sealing composition in drilling fluid and the fracture is sealed, thereby strengthening the wellbore.

An alternate embodiment of the present invention provides a method for sealing a fracture in a weak wellbore, wherein the method has three components including characterizing a fracture; characterizing a fracture sealing composition; and implementing the fracture sealing. The first component, characterizing a fracture, provides the first of the three steps of the method. In the first step, a fracture width is selected based on the existing or desired shale shaker screen mesh size and/or available sealing particulates so that the sealing particulates can pass through the shaker screen with the drilling fluid without being discarded together with the drill cuttings.

Optionally, a standard fracture width may be selected, e.g., 300 microns. Based on the selected fracture width, the second step includes defining an optimized fracture sealing composition. Optionally, the same fracture sealing composition is used for the same selected fracture width. The third step includes defining the spurt loss volume of the particulate fracture sealing fluid including the fracture sealing composition at various concentrations by testing the fracture sealing composition in a fluid.

The second component of the embodiment includes characterizing a fracture. Steps four and five of the method are included in the second component. The fourth step of the method includes collecting related data needed for treating a weak formation. Based on the selected fracture width and the collected data, the fifth step included determining the fracture volume capacity for the weak wellbore to be strengthened.

The third component of the embodiment, implementing the fracture sealing, includes steps six through nine of the method. In step six, based on the determined fracture volume capacity, the concentration of the fracture sealing composition is defined so that the spurt loss volume of the fracture sealing fluid is less than or equal to the fracture volume capacity. Step seven includes transporting the fracture sealing composition to the rig site. In step eight, the fracture sealing composition is added to the drilling fluid according to the defined concentration. The weak zone is then treated with the particulate fracture sealing fluid in step nine. The shale shaker screen does not have to be changed in this embodiment when drilling conditions are changed since the particulate sizes are not changed but only concentration of the fracture sealing composition is changed.

In the embodiment of the directly aforementioned method, a change deemed necessary before step nine is finished only impacts step four or the collected data and the concentration of the fracture sealing composition of steps five and six. For example, when a higher drilling fluid circulation rate is implemented, a higher wellbore pressure and a smaller fracture volume capacity is created for the weak formation. Therefore, a higher concentration of the sealing composition corresponding to a spurt loss volume less than or equal to this new and smaller fracture volume capacity can be used. This can be easily implemented at a rig site by simply adding more of the same fracture sealing composition. If less of the fracture sealing composition is needed, this can be achieved by simply adding more drilling fluid to dilute the concentration. The fracture sealing composition is still optimized for the fracture sealing width and the shale shaker screen does not have to be changed. Steps one through three are never affected.

In one embodiment, the fracture sealing width is first selected based on at least one of the factors such as fracture length, wellbore radius, flow restrictions, pressure, formation mechanical properties, deviation, temperature, stress, sealing particulates, fluid for using the sealing particulates in and/or shale shaker screens. Based on the fracture sealing width, a fracture volume capacity is defined. Then a fracture sealing fluid that has a spurt loss volume less than or equal to the fracture volume capacity is defined. A fracture sealing composition is then manufactured. The fracture sealing composition is then transported the rig site. The facture sealing composition is circulated in wellbore fluid thereby creating the fracture sealing fluid to the weak wellbore.

EXAMPLES

The following examples are illustrative of the principles of this invention. It is understood that this invention is not limited to any one specific embodiment exemplified herein, whether in the examples or the remainder of this patent application.

Example 1

In an example of an embodiment of the present invention, a vertical wellbore of 8.5 inches in diameter is to be drilled in a weak subterranean formation. The isotropic horizontal stress is 5000 psi. In order to balance the formation for wellbore stability, the wellbore pressure has to be maintained at 5500 psi. Without a wellbore strengthening treatment, it is very likely the higher wellbore pressure will fracture the weak formation causing lost circulation during drilling.

To apply the wellbore strengthening method, a 350 micron fracture sealing width is selected partially because an API 40 mesh shale shaker screen is desirable so that cuttings that will not pass through the screen can be separated out of the drilling fluid system to avoid deterioration of the fluid properties during drilling. This will allow the selected particles passing the screen with the drilling fluid without being discarded together with the drilled cuttings.

Based on the fracture sealing width 350 micron, an optimized standard fracture sealing composition is defined. A standard sealing composition for 350 micron fracture and API 40 mesh screens can be made available for any use. The unit slot length spurt loss volume of the fluid of the standard composition at various concentrations is defined by testing the sealing composition in a drilling fluid. A particulate fracture sealing composition in a 9 pound per barrel weight water based drilling fluid has been characterized with a slot disk with a slot of 350 micron wide on API PPA.

Needed data for drilling into the weak formation is then collected. The Young's modulus of the weak formation is 1,000,000 psi and Poisson's ratio is 0.25 based on lab tests on core samples. Based on the fracture width of 350 microns, the unit height fracture volume capacity is determined for the weak wellbore to be strengthened. The unit height fracture volume capacity is calculated by applying Equation 2, 3, 4 and 8. The calculated volume is 0.041 inch$^3$/inch. Based on the determined fracture volume capacity, the concentration of the standard fracture sealing composition is determined so that the unit slot length spurt loss volume of the fracture sealing fluid is not larger than the unit height fracture volume capacity. The fracture sealing composition has different unit slot length spurt loss volumes at different concentrations as shown in FIG. 6. From FIG. 6, it may be determined that a particulate concentration of 33 pound per barrel can have a unit slot length spurt loss volume of about 0.041 inch$^3$/inch or smaller. For safety due to uncertainties, a 35 pound per barrel of the particulate composition can be selected for making the particulate fracture sealing fluid for drilling. The final fluid made by a rig drilling fluid can be further verified by Permeability Plugging Apparatus (PPA) tests.

The fracture sealing composition is then transported to the rig site and added to the drilling fluid according to the defined concentration. The weak zone is then drilled with the particulate fracture sealing fluid, wherein API 40 mesh shale shaker screen can be used. During drilling with the particulate sealing fluid, the required spurt loss control can be monitored by testing the fluid with a slot disk with slots of 350 micron wide. This quality control can ensure the designed function is met all time at the rigsite. If the spurt loss volume is increasing approaching the desired level during drilling, more particulates can be added into the fluid to tighten up the control.

After the fluid has been treated with 35 pounds of the particulate sealing composition but before drilling the weak interval, it is decided to implement a higher circulation rate of the drilling fluid. Higher wellbore pressure of 5800 psi will be created when the higher drilling fluid circulation rate is implemented. Based on the changed condition, a new unit height fracture volume capacity for the weak formation is calculated based on the same 350 micron fracture sealing width. Because the wellbore pressure of 5800 psi is higher than the previous 5500 psi, the new smaller unit height fracture volume capacity for the weak formation will be smaller. The new unit height fracture volume capacity is calculated to be 0.019 inch$^3$/inch. A higher concentration of the sealing composition corresponding to this smaller unit slot length spurt loss volume that is less than or equal to the new and smaller unit height fracture volume capacity is defined. Based on FIG. 6, this change can be adapted with a 58 pound per barrel particulate concentration for making the particulate fracture sealing fluid for the drilling. At the rig site, additional 23 pound per barrel fracture sealing composition is added to the drilling fluid. The composition is still an optimized one and API 40 mesh shale shaker screens can still be used. Similarly, the quality control on spurt loss control can be done with the same slot disk of slots of 350 micron wide.

Right before the weak zone has been drilled through, a better data point of Young's modulus of 1,200,000 psi is obtained. A new unit height fracture volume capacity of 0.026 inch$^3$/inch for the weak formation is then calculated based on the same 350 micron fracture sealing width and the larger Young's modulus. A concentration of 45 pound per barrel of the sealing composition corresponding to a new unit slot length spurt loss volume that is less than or equal to the new and larger unit height fracture volume capacity is defined. At the rig site, the fracture sealing fluid is simply diluted by adding more drilling fluid. The composition is still an optimized one and no shale shaker screen needs to be changed. Optionally, in this case, the fluid can be used without dilution because it controls a smaller spurt loss volume that still satisfies the required criterion.

Example 2

In subterranean formations, rock properties can vary when different thick and thin formation layers are penetrated by a drill bit during drilling. Drilling parameters, such as weight on bit, rotation speeds, and pump rates, are often adjusted to maximize the rate of penetration for different formations. At different rates of penetration, the amount of cuttings generated and carried by drilling fluid in the annulus also varies, together with pump rates, affecting wellbore pressure while drilling. Such data is often dynamic throughout the drilling of the well. At least in part due to such varying conditions, many rigs presently incorporate technology wherein the rig operators can acquire and observe the constantly changing data at real time through such means, for example, as logging while drilling (LWD), measurement while drilling (MWD), and surface data logging tools. The data acquired can be translated into other useful data to guide the drillers to optimize the drilling parameters or make other decisions.

However, with the aforementioned method known in the art wherein the fracture is necessarily propped, the value of access to real time data can be diminished due to constraints inherent in the conventional method. The fracture width is based upon one or more varying parameters including formation properties, drilling parameters and wellbore properties. The varying parameters create difficulties in the known method in attempts to optimize sealing while drilling at real time, because the determined fracture propping width will change frequently. To adapt to the changes of fracture propping width and still maintain an optimized sealing to the fractures, the fracture sealing composition has to be changed accordingly with different sizes of particles.

In this conventional method, because the fracture propping width is always unknown before other parameters are defined, various particle sizes such as 100, 200, 300, 400, 500, 600, 700, 800, 900 and 1000 micron, many of which may not be useful for the entire drilling, have to be available to prepare for an optimized composition for an unknown real time changing fracture propping width. The stocked particles at a rig site may have to be many times what is really needed just to ensure a particle size will be available when needed. Such preparation often is difficult at a rig site due to the large quantity of composition required. When the fracture propping width is unknown ahead of time, it can be difficult to determine the type and quantity of composition needed. To optimize propping, when a larger fracture width is calculated, larger particles have to be added to alter the particle size distribution toward the new and larger fracture propping width. It is difficult to satisfy the needed concentration and packing efficiency at the same time; therefore, the needed concentration or packing efficiency may have to be compromised. It is impossible to have a supply of continuous particle sizes. It is likely the needed size is not available and the formulation has to be compromised.

Additionally, in the conventional method, the particle size change will also impact the solid control system for separating the drilling cuttings from the drilling fluid. For example, during drilling with a particulate fracture propping fluid, when a higher wellbore pressure is implemented to the wellbore, this pressure data together with other necessary data can be fed into a computer model. Then a wider fracture propping width, for example, of 318 micron is calculated. Then a decision has to be made for selecting a particle size. For example, when there are particulates of average sizes of 100, 200, 300, 400, 500, 600, 700, 800, 900 and 1000 micron at the rig site, generally the 400 micron composition will be added to the existing fluid, which is larger than needed and not optimized. If the shale shaker screen was previously optimized for letting smaller than average 300 micron particles to pass, the screen would have to be changed to let average 400 micron particles pass therethrough. When there is no such a screen mesh available, a compromised screen has to be implemented. Having different shale shaker screens stocked at the rig site together with all possible sizes of particulates for fracture sealing is generally a large burden financially and logistically.

Furthermore, in the conventional method, direct quality control may not be done at the rig site due to the time constraint and availability of the apparatus. Having a convenient way to implement these into an automatic system according to the change of the fracture propping width can be physically difficult.

Comparatively, in the method disclosed in at least one embodiment of the present invention, a fracture sealing width for a fracture to be sealed can be selected independently of formation properties, wellbore properties and drilling parameters, and continuous fracture sealing can be implemented easily at or near real time. Such a method allows a single fracture sealing width to be selected for drilling through varying formations. A fracture sealing composition for optimally sealing the selected fracture sealing width can be selected and tested ahead of time for defining unit slot length spurt loss volumes at various concentrations in a drilling fluid. During drilling, a computer model can be utilized to process the acquired data for the unit height fracture volume capacity at real time based on the selected fracture sealing width. The calculated real time unit height fracture volume capacities for different layers of formations can be tied directly to the concentrations of the fracture sealing composition so that the unit slot length spurt loss volume is less than or equal to the unit height fracture volume capacity for each layer. In other words, a needed change in the fracture sealing capacity can be easily achieved by changing the concentration of the fracture sealing composition, and the sealing relationship between the fracture width and the composition is still optimized.

In this method, no solid control system, such as shale shaker screens, needs to be changed out because the particle size distribution is not changed by only changing the particulate concentration. For example, when a higher wellbore pressure is implemented to the wellbore, the pressure data together with other necessary data can be fed into the computer model. Then, a smaller fracture volume capacity is calculated. With this smaller fracture volume capacity and a possible safety factor, a new and higher concentration of the fracture sealing composition is determined. Based on the current concentration of the fracture sealing composition in the drilling fluid, the pump rate, and the total drilling fluid volume, the total additional amount of the fracture sealing composition to be added at a calculated rate is determined. The information regarding the additional amount needed can then be passed to an automation system that controls adding the sealing composition from a silo. At a rig site, one type of sealing composition and one size shale shaker screen mesh are sufficient for all different layers of formations at various conditions. The unit slot length spurt loss volume can be quality controlled ahead of time to ensure the sealing effectiveness. The entire process can be implemented and accomplished smoothly and successfully.

The various embodiments of the present invention can be joined in combination with other embodiments of the invention and the listed embodiments herein are not meant to limit the invention. All combinations of various embodiments of the invention are enabled, even if not given in a particular example herein.

As used herein, the term "fracture sealing composition" or "sealing composition" or "composition" refers to one or more particulates for sealing a fracture.

As used herein, the term "fracture sealing fluid" or "sealing fluid" refers to any particulate fluid comprising one or more particulates for sealing a fracture.

As used herein, the term "formulation" refers to any sealing fluid comprising one or more particulates for sealing a fracture.

As used herein, the term "base fluid" refers to any fluid that is used to make a sealing fluid with a fracture sealing composition.

As used herein, the term "wellbore fluid" refers to any fluid that can exist in a wellbore. It includes but not limited to drilling fluid, cementing slurry, spacer fluid, drill-in fluid, completion fluid, workover fluid, oil, water or brine.

As used herein, the term "bridging particle" refers to one or more particulates of the fracture sealing composition sized equivalently to or larger than the selected fracture sealing width.

As used herein, the term "evaluate" refers to the step of estimating or calculating a numerical value based upon stipulated assumptions.

Use of the term "optionally" with respect to any element of a claim is intended to mean that the subject element is permitted but not required.

Each and every printed publication referred to above is incorporated herein by reference in its entirety to the fullest extent permitted as a matter of law.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What I claim is:

1. A method for improving wellbore pressure containment comprising:
   a) selecting a fracture sealing width of a fracture connecting to a wellbore in a formation;
   b) defining a particulate fracture sealing composition;
   c) determining a spurt loss volume for the fracture sealing width at different concentrations of the defined particulate fracture sealing composition in a fluid;
   d) evaluating a fracture volume capacity by:

i) computing the values of $L = \sqrt{\left(\frac{W(R) \cdot E}{4(1-v^2)\Delta P}\right)^2 + R^2}$ where W(R) is the selected fracture sealing width at the fracture mouth, R is the wellbore radius, v is a Poisson's ratio of the formation, E is a Young's modulus of the formation, L is the distance from the center of the wellbore to the fracture tip, and $\Delta P$ is the net pressure of fracture pressure above the fracture closing stress;

ii) computing the value of $$W(x) = \frac{4(1-v^2)\Delta P}{E}\sqrt{L^2 - x^2}$$

where W(x) is an inflated fracture width at a location x between the fracture mouth and the fracture tip;
   iii) computing the value of $A = \int_R^L W(x)dx$
   where A is a pressurized fracture cross section area; and
   iv) computing the value of fracture volume capacity $Vc = A \cdot H$
   wherein H is a fracture height of the fracture; and
   e) selecting a concentration of the sealing composition for particulate fracture sealing fluid wherein the spurt loss volume for the sealing fluid is less than or equal to the fracture volume capacity.

2. The method of claim 1 further comprising mixing and circulating the particulate fracture sealing fluid in the wellbore.

3. The method of claim 1 further comprising varying the concentration of the fracture sealing composition in the sealing fluid to ensure that the relationship between the particle size distribution of the fracture sealing composition and the fracture sealing width remains constant in a changed wellbore condition.

4. The method of claim 1 further comprising manufacturing the sealing composition.

5. The method of claim 4 further comprising specifying at least one of the following of the fracture sealing composition:

sealing particle size, particle type, particle composition, particle strength and particle density.

6. The method of claim 4 further comprising manufacturing the sealing composition through at least one of the following: a crusher, a sizing screen, a blender, a pump, or holding tank.

7. A method for improving wellbore pressure containment comprising:
   a) selecting a fracture sealing width of a fracture connecting to a wellbore in a formation;
   b) evaluating a fracture volume capacity by:
      I) computing the value of $$L = \sqrt{\left(\frac{W(R) \cdot E}{4(1-v^2)\Delta P}\right)^2 + R^2}$$

where W(R) is the selected fracture sealing width at the fracture mouth, R is the wellbore radius, v is a Poisson's ratio of the formation, E is a Young's modulus of the formation, L is the distance from the center of the wellbore to the fracture tip, and ΔP is the net pressure of fracture pressure above the fracture closing stress;
      II) computing the value of $$W(x) = \frac{4(i-v^2)\Delta P}{E}\sqrt{L^2 - x^2}$$

where W(x) is an inflated fracture width at a location x between the fracture mouth and the fracture tip;
      III) computing the value of $A = \int_R^L W(x)dx$
   where A is a pressurized fracture cross section area; and
      IV) computing the value of fracture volume capacity Vc=A·H
   wherein H is a fracture height of the fracture;
   c) formulating a fracture sealing fluid for sealing the selected fracture sealing width by adding to a fluid large, medium and small particulates in which at least one or more of the large particulates is larger than the selected fracture sealing width to seal the fracture at the selected fracture sealing width, provided that a spurt loss volume of the fracture sealing fluid is less than or equal to the fracture volume capacity of the fracture; and
   d) pumping the fracture sealing fluid into the wellbore.

8. The method of claim 7 further comprising selecting the fracture sealing width of the fracture connecting to the wellbore based on at least one factor selected from the group consisting of fracture length, wellbore radius, flow restrictions, tools, possible mechanical interference to moving parts of a tool, pressure, strengthening effects, formation mechanical properties, deviation, temperature, stress, sealing particulates, fluid for using the sealing particulates, or shale shaker screens.

9. The method of claim 7 further comprising selecting the fracture sealing width at a mouth of the fracture.

10. The method of claim 7 further comprising measuring the spurt loss volume against a filtration medium with at least one slot that has a slot width equivalent to the selected fracture sealing width.

11. The method of claim 7 further comprising adding particulates to the fracture sealing fluid selected from the group consisting of calcium carbonate, sand, coke, petroleum coke, graphite, resilient graphitic carbon, synthetic graphite, cedar fiber, nut hulls, corn cobs, fiber, synthetic fiber, paper, threaded paper, ground paper, carbon fiber, threaded rug, asphalt, gilsonite, rubber, foam rubber, drilled cuttings, saw dust, mica, wood chips, engineering plastics, hollow spheres, fly ash, hollow plastic spheres, hollow glass spheres, cotton seed hulls, walnut hulls, pistachio hulls, almond hulls, peanut hulls, cement, clay, bentonite, modified clay, organoclay, limestone, dolomite, marble, resin particles, metal particles, ceramic particles, nanotechnology particles, barite, hematite, iron oxide, ilmenite, and combinations thereof.

12. A method for improving wellbore pressure containment comprising:
   a) selecting a particulate fracture sealing composition;
   b) determining a fracture sealing width of a fracture connecting to the wellbore in a formation to be sealed based on at least a particle size of the selected particulate fracture sealing composition;
   c) determining a fracture volume capacity of the fracture based on factors including the fracture sealing width by:

i) computing the values of $L = \sqrt{\left(\frac{W(R) \cdot E}{4(1-v^2)\Delta P}\right)^2 + R^2}$ where W(R) is the fracture sealing width at the fracture mouth, R is the wellbore radius, v is a Poisson's ratio of the formation, E is a Young's modulus of the formation, L is the distance from the center of the wellbore to the fracture tip, and ΔP is the net pressure of fracture pressure above the fracture closing stress;
   ii) computing the value of $$L = \sqrt{\left(\frac{W(R) \cdot E}{4(1-v^2)\Delta P}\right)^2 + R^2}$$

where W(x) is an inflated fracture width at a location x between the fracture mouth and the fracture tip;
   iii) computing the value of $A = \int_R^L W(x)dx$
   where A is a pressurized fracture cross section area; and
   iv) computing the value of fracture volume capacity Vc=A·H
   wherein H is a fracture height of the fracture;
   d) formulating a fracture sealing fluid with the particulate fracture sealing composition at a concentration in a fluid, provided that a spurt loss volume of the fracture sealing fluid is less than or equal to the fracture volume capacity; and
   e) pumping the fracture sealing fluid into the wellbore.

13. The method of claim 12, wherein the spurt loss volume is measured against a filtration medium with at least one slot that has a slot width equivalent to the determined fracture sealing width.

14. The method of claim 12, wherein the spurt loss volume is a unit slot length spurt loss volume and the fracture volume capacity is a unit height fracture volume capacity.

15. The method of claim 12 further comprising manufacturing the sealing composition through at least one of a crusher, a sizing screen, and a blender.

16. The method of claim 12 further comprising varying the concentration of the fracture sealing composition in the fracture sealing fluid to ensure that the particulate fracture sealing fluid has a spurt loss volume less than or equal to the fracture volume capacity.

17. The method of claim 12 further comprising determining the fracture sealing width at a mouth of the fracture.

18. The method of claim 12 wherein the fluid comprises a solid free fluid, a drilling fluid, a completion fluid, a spacer fluid, a cement slurry, water, brine, sea water, salt water, oil, synthetic oil, or a workover fluid.

19. The method of claim 12 wherein a volume of the particulates that have at least one dimension of a range of 100 to 150 percent of a selected fracture sealing width is 5 to 35 percent of the total volume of all the sealing particulates in the sealing fluid.

* * * * *